United States Patent
Orlov et al.

(10) Patent No.: US 11,583,394 B2
(45) Date of Patent: *Feb. 21, 2023

(54) METHODS FOR DEPLOYING A PROSTHETIC MITRAL VALVE

(71) Applicant: Tel HaShomer Medical Research Infrastructure and Services Ltd., Ramat-Gan (IL)

(72) Inventors: Boris Orlov, Haifa (IL); Ehud Raanani, Hod-HaSharon (IL)

(73) Assignee: Tel HaShomer Med. Rsch. Infra. and Services Ltd., Ramat-Gan (IL)

( * ) Notice: Subject to any disclaimer, the term of this patent is extended or adjusted under 35 U.S.C. 154(b) by 674 days.

This patent is subject to a terminal disclaimer.

(21) Appl. No.: 16/655,656

(22) Filed: Oct. 17, 2019

(65) Prior Publication Data
US 2020/0046491 A1 Feb. 13, 2020

Related U.S. Application Data

(62) Division of application No. 13/475,994, filed on May 20, 2012, now Pat. No. 10,500,038.

(60) Provisional application No. 61/488,180, filed on May 20, 2011.

(51) Int. Cl.
*A61F 2/24* (2006.01)
*A61F 2/95* (2013.01)

(52) U.S. Cl.
CPC .......... *A61F 2/2409* (2013.01); *A61F 2/2427* (2013.01); *A61F 2/95* (2013.01)

(58) Field of Classification Search
CPC ........ A61F 2/2409; A61F 2/2427; A61F 2/95; A61F 2/24; A61F 2220/0008; A61F 2/0016; A61F 2220/0075; A61F 2250/0007; A61F 2250/0008; A61F 2250/006

See application file for complete search history.

(56) References Cited

U.S. PATENT DOCUMENTS

| | | |
|---|---|---|
| 7,018,408 B2 | 3/2006 | Bailey et al. |
| 7,621,948 B2 | 11/2009 | Herrmann et al. |
| 7,753,949 B2 | 7/2010 | Lamphere et al. |
| 8,070,802 B2 | 12/2011 | Lamphere et al. |

(Continued)

FOREIGN PATENT DOCUMENTS

| | | |
|---|---|---|
| CA | 2898991 A1 | 8/2014 |
| CN | 101180010 A | 5/2008 |

(Continued)

OTHER PUBLICATIONS

Advisory Action for U.S. Appl. No. 14/402,387 dated Mar. 1, 2018.

(Continued)

*Primary Examiner* — Paul B Prebilic
(74) *Attorney, Agent, or Firm* — Dorsey & Whitney LLP

(57) ABSTRACT

According to an aspect of some embodiments of the invention, there is provided a method of deploying an expandable prosthetic mitral valve in a subject, the method comprising: deploying a first component of the prosthetic mitral valve in a left atrium; deploying a second component of the prosthetic mitral valve in a left ventricle; and approximating the first and the second components so that leaflets of a native mitral valve are trapped between the first and the second components.

15 Claims, 22 Drawing Sheets

(56) References Cited

U.S. PATENT DOCUMENTS

| | | | |
|---|---|---|---|
| 8,870,950 | B2 | 10/2014 | Hacohen |
| 9,364,326 | B2 | 6/2016 | Yaron |
| 9,700,412 | B2 | 7/2017 | Yaron et al. |
| 9,949,830 | B2 | 4/2018 | Solem |
| 10,130,471 | B2 | 11/2018 | Keränen et al. |
| 10,292,816 | B2 | 5/2019 | Raanani et al. |
| 10,292,850 | B2 | 5/2019 | Vad et al. |
| 11,065,114 | B2 | 7/2021 | Raanani et al. |
| 2002/0006554 | A1 | 1/2002 | Fischer et al. |
| 2002/0065554 | A1 | 5/2002 | Streeter |
| 2003/0014104 | A1 | 1/2003 | Cribier |
| 2003/0083742 | A1* | 5/2003 | Spence ............... A61F 2/2445 623/2.16 |
| 2004/0138745 | A1 | 7/2004 | Macoviak et al. |
| 2006/0195134 | A1 | 8/2006 | Crittenden |
| 2006/0195184 | A1* | 8/2006 | Lane .................. A61F 2/2418 623/2.38 |
| 2006/0241745 | A1 | 10/2006 | Solem |
| 2007/0016288 | A1 | 1/2007 | Gurskis et al. |
| 2007/0050020 | A1 | 3/2007 | Spence |
| 2007/0260305 | A1* | 11/2007 | Drews ................ A61F 2/2427 623/2.11 |
| 2008/0039935 | A1 | 2/2008 | Buch et al. |
| 2009/0192585 | A1 | 7/2009 | Bloom et al. |
| 2009/0192586 | A1 | 7/2009 | Tabor et al. |
| 2009/0198324 | A1* | 8/2009 | Orlov ................. A61F 2/2445 623/2.37 |
| 2010/0022640 | A1 | 1/2010 | Stoutamire |
| 2010/0042208 | A1 | 2/2010 | Herrmann et al. |
| 2010/0049313 | A1 | 2/2010 | Alon et al. |
| 2010/0249923 | A1 | 9/2010 | Alkhatib et al. |
| 2010/0331971 | A1 | 12/2010 | Keraenen et al. |
| 2011/0137397 | A1 | 6/2011 | Chau et al. |
| 2011/0137410 | A1 | 6/2011 | Hacohen |
| 2011/0224785 | A1 | 9/2011 | Hacohen |
| 2011/0264208 | A1 | 10/2011 | Duffy et al. |
| 2012/0010461 | A1 | 1/2012 | Goldfarb et al. |
| 2012/0022640 | A1 | 1/2012 | Gross et al. |
| 2012/0101571 | A1 | 4/2012 | Thambar et al. |
| 2014/0088695 | A1 | 3/2014 | Figulla et al. |
| 2014/0222136 | A1 | 8/2014 | Geist et al. |
| 2015/0045880 | A1 | 2/2015 | Hacohen |
| 2015/0173897 | A1 | 6/2015 | Raanani et al. |
| 2015/0351903 | A1 | 12/2015 | Morriss et al. |
| 2015/0351908 | A1 | 12/2015 | Kernen et al. |
| 2015/0374493 | A1 | 12/2015 | Yaron et al. |
| 2016/0095705 | A1 | 4/2016 | Keränen et al. |
| 2017/0128199 | A1 | 5/2017 | Gurovich et al. |
| 2018/0014932 | A1 | 1/2018 | Hammer et al. |
| 2019/0083245 | A1 | 3/2019 | Hariton et al. |
| 2019/0125534 | A1 | 5/2019 | Arcaro et al. |
| 2020/0197175 | A1 | 6/2020 | Chang et al. |

FOREIGN PATENT DOCUMENTS

| | | |
|---|---|---|
| CN | 102292053 A | 12/2011 |
| CN | 102438546 A | 5/2012 |
| DE | 102006052564 | 12/2007 |
| EP | 2948102 B1 | 1/2019 |
| EP | 2852354 B1 | 5/2020 |
| JP | 2008536592 A | 9/2008 |
| JP | 2011509806 A | 3/2011 |
| JP | 2012500665 A | 1/2012 |
| JP | 2012521222 A | 9/2012 |
| JP | 7051736 B2 | 4/2022 |
| WO | 0060995 A2 | 10/2000 |
| WO | 2005087140 A1 | 9/2005 |
| WO | 2006116558 A2 | 11/2006 |
| WO | 2007135101 A1 | 11/2007 |
| WO | 2009134701 A2 | 11/2009 |
| WO | 2010108079 A1 | 9/2010 |
| WO | 2012095116 A1 | 7/2012 |
| WO | 2013175468 A2 | 11/2013 |
| WO | 2014114795 A1 | 7/2014 |
| WO | 2018112429 A1 | 6/2018 |
| WO | 2020092096 A2 | 5/2020 |
| WO | 2020100050 A1 | 5/2020 |
| WO | 2021028867 A1 | 2/2021 |
| WO | 2022090881 A1 | 5/2022 |
| WO | 2022090882 A1 | 5/2022 |

OTHER PUBLICATIONS

Applicant-Initiated Interview Summary for U.S. Appl. No. 14/402,387 dated Dec. 28, 2017.
Applicant-Initiated Interview Summary for U.S. Appl. No. 14/402,387 dated May 25, 2017.
Australian Examination Report for Australian Application No. 2013264730 dated Dec. 20, 2017.
Australian Examination Report for Australian Application No. 2013264730 dated Jan. 13, 2017.
Chinese Notification of Office Action and English Translation for Chinese Application No. 201380038199.0 dated Dec. 14, 2016.
Chinese Notification of Office Action and Search Report for Chinese Application No. 201380038199.0 dated Sep. 7, 2016.
Chinese Translation of Notification of Office Action and Search Report and for Chinese Application No. 201380038199.0 dated Sep. 7, 2016.
Chinese Translation of Notification of Office Action for Chinese Application No. 201380038199.0 dated Dec. 3, 2015.
Communication Relating to the Results of the Partial International Search from the International Application No. PCT/IL2013/050432 dated Nov. 18, 2013.
European Communication Pursuant to Article 94(3) EPC for European Application No. 13732633.6 dated Jan. 8, 2018.
Final Office Action for U.S. Appl. No. 13/083,643 dated Mar. 5, 2014.
Final Office Action for U.S. Appl. No. 13/475,994 dated Jan. 10, 2017.
Final Office Action for U.S. Appl. No. 13/475,994 dated Jun. 10, 2015.
Final Office Action for U.S. Appl. No. 13/475,994 dated Jun. 8, 2018.
Final Office Action for U.S. Appl. No. 14/402,387 dated Oct. 2, 2017.
International Preliminary Report on Patentability from International Application No. PCT/IL2013/050432 dated Dec. 4, 2014.
International Search Report and the Written Opinion from International Application No. PCT/IL2013/050432 dated Feb. 26, 2014.
Japanese Notice of Reason for Rejection for Japanese Application No. 2015-513347 dated Feb. 14, 2017.
Japanese Translation of Notice of Reason for Rejection for Japanese Application No. 2015-513347 dated Feb. 14, 2017.
Non-Final Office Action for U.S. Appl. No. 13/475,994 dated Apr. 1, 2016.
Non-Final Office Action for U.S. Appl. No. 13/475,994 dated Dec. 28, 2018.
Non-Final Office Action for U.S. Appl. No. 13/475,994 dated Oct. 1, 2014.
Non-Final Office Action for U.S. Appl. No. 13/475,994 dated Sep. 11, 2017.
Notice of Allowance for U.S. Appl. No. 13/475,994 dated Jul. 22, 2019.
Notice of Amendment and English Translation for Chinese Application No. 201710425696.6 dated Jun. 23, 2017.
Restriction Requirement for U.S. Appl. No. 13/475,994 dated Mar. 11, 2014.
U.S. Appl. No. 13/475,994, filed May 20, 2012.
U.S. Appl. No. 61/488,180, filed May 20, 2011.
Office Action for Japanese Application No. 2019/032726 dated Jan. 19, 2021.
Issue Notification for U.S. Appl. No. 13/475,994, dated Nov. 20, 2019.
Translation of: Office Action for Chinese Application No. 201380038199.0 dated Dec. 3, 2015.
Communication Pursuant to Rule 94(3) for European Patent Application No. 20760551.0 dated Apr. 7, 2022.

(56) References Cited

OTHER PUBLICATIONS

International Search Report and Written Opinion for International Application No. PCT/IB2021/059798 dated Jan. 24, 2022.
International Search Report and Written Opinion for International Application No. PCT/IB2021/059799 dated Jan. 25, 2022.
Office Action for Japanese Application No. 2019/032726 dated Nov. 19, 2021.
U.S. Appl. No. 17/263,776, filed Jan. 27, 2021.
U.S. Appl. No. 62/767,018, filed Nov. 14, 2018.

* cited by examiner

METHODS FOR DEPLOYING A PROSTHETIC MITRAL VALVE

RELATED APPLICATIONS

This application is a divisional of U.S. patent application Ser. No. 13/475,994 to Orlov et al., filed May 20, 2012, which issued as U.S. Pat. No. 10,500,038 on Dec. 10, 2019, and which claims the benefit of U.S. Provisional Patent Application No. 61/488,180 to Orlov et al., filed May 20, 2011, the contents of which are incorporated herein by reference in their entirety.

FIELD AND BACKGROUND OF THE INVENTION

The present invention relates to the field of cardiac surgery, and more particularly to the field of prosthetic heart valves, especially prosthetic mitral valves.

The human heart 10, depicted in cross-sectional long axis view in FIGS. 1A (during diastole) and 1B (during systole), is a muscular organ that pumps deoxygenated blood through the lungs to oxygenate the blood and pumps oxygenated blood to the rest of the body by rhythmic contractions of four chambers.

After having circulated in the body, deoxygenated blood from the body enters right atrium 12 through vena cava 14. Right atrium 12 contracts, pumping the blood through a tricuspid valve 16 into right ventricle 18, FIG. 1A. Right ventricle 18 contracts, pumping the blood through a pulmonary semi-lunar valve 20 into the pulmonary artery 22 which splits to two branches, one for each lung, FIG. 1B. The blood is oxygenated while passing through the lungs and reenters the heart to the left atrium 24. Left atrium 24 contracts, pumping the oxygenated blood through the mitral valve 26 into the left ventricle 28, FIG. 1A. Left ventricle 28 contracts, pumping the oxygenated blood through the aortic valve 30 into the aorta 32 to be distributed to the rest of the body, FIG. 1B.

In mitral valve 26, an approximately circular mitral annulus 34 defines a mitral valve orifice 36. Attached to the periphery of mitral annulus 34 is an anterior leaflet 38 and a smaller posterior leaflet 40, leaflets 38 and 40 connected to papillary muscles 44 at the bottom of left ventricle 28 by chordae 46. The typical area of the mitral lumen in a healthy adult is between 4 and 6 cm$^2$ while the typical total surface area of leaflets 38 and 40 is significantly larger, approximately 12 cm$^2$.

During diastole depicted in FIG. 1A, left atrium 24 contracts to pump blood into left ventricle 28 through orifice 36 of mitral valve 26. The blood flows through orifice 36, pushing leaflets 38 and 40 into left ventricle 28 with little resistance. The leaflets of aortic valve 30 are kept closed by blood pressure in aorta 32.

During systole, depicted in FIG. 1B, left ventricle 28 contracts to pump blood into aorta 32 through aortic valve 30 which leaflets are pushed open by the blood flow with relatively little resistance. Mitral annulus 34 contracts, pushing leaflets 38 and 40 inwards and reducing the area of mitral valve orifice 36 by about 20% to 30%. Papillary muscles 44 contract, maintaining the tension of chordae 46 and pulling the edges of leaflets 38 and 40, preventing prolapse of leaflets 38 and 40 into left atrium 24. Leaflets 38 and 40 curve into left ventricle 28 and coapt to accommodate the excess leaflet surface area, producing a coaptation surface 42 that constitutes a seal. The typical length of coaptation surface 42 in a healthy heart 10 of an adult is approximately 7-8 mm. The pressure of blood in left ventricle 28 pushes against the ventricular surfaces of leaflets 38 and 40, tightly pressing leaflets 38 and 40 together at coaptation surface 42 so that a tight leak-proof seal is formed.

An effective seal of mitral valve 26 during ventricular systole is dependent on a sufficient degree of coaptation, in terms of length, area and continuity of coaptation surface 42. If coaptation surface 42 is insufficient or non-existent, there is mitral valve insufficiency, that is, regurgitation of blood from left ventricle 28 into left atrium 24 during ventricular systole. A lack of sufficient coaptation may be caused by any number of physical anomalies that allow leaflet prolapse (e.g., elongated or ruptured chordae 46, weak papillary muscles 44) or prevent coaptation (e.g., short chordae 46, small leaflets 38 and 40). There are also pathologies that lead to a mitral valve insufficiency including collagen vascular disease, ischemic mitral regurgitation (resulting, e.g., from myocardial infarction, chronic heart failure, or failed/unsuccessful surgical or catheter revascularization), myxomatous degeneration of leaflets 38 and 40 and rheumatic heart disease. Mitral valve insufficiency leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

Apart from humans, mammals that suffer from mitral valve insufficiency include horses, cats, dogs, cows, sheep and pigs.

It is known to use open-heart surgical methods to treat mitral insufficiency, for example by modifying the subvalvular apparatus (e.g., lengthening or shortening chordae 46) to improve leaflet coaptation, implanting an annuloplasty ring to force mitral valve annulus 34 into a normal shape.

Aortic valves are known to suffer from aortic insufficiency or aortic stenosis. It is known to deploy a prosthetic aortic valve using minimally invasive surgery to replace a malfunctioning native aortic valve. Typically, an expandable frame (e.g., a stent or a ring) supporting artificial aortic leaflets is positioned inside the orifice of an aortic valve, typically endovascularly with a catheter passing through the aorta, but also transapically through a hole near the apex of the heart, passing into left ventricle 28. The frame is expanded across the aortic annulus folding and overlying the native aortic valve leaflets, maintaining the prosthetic aortic valve in place by exertion of an axial force and by adopting an "hourglass" shape that distributes axial forces on the native aortic valve annulus and the surrounding tissue. Commercially available prosthetic aortic valves include the Lotus™ by Sadra Medical (Campbell, Calif., USA) and the CoreValve™ by Medtronic (Minneapolis, Minn., USA).

It has been suggested to deploy a prosthetic mitral valve, analogous to a prosthetic aortic valve. A challenge to implementing such suggestions is retention of the prosthesis in place during ventricular systole. Unlike the aortic valve annulus that constitutes a stable anchoring feature, especially when calcified, the mitral valve annulus is not a sufficiently stable anchoring feature (less than half of the mitral valve annulus is of fibrotic tissue) and is dynamic (changing size and shape as the heart beats). Further, unlike the aortic valve that is open during ventricular systole, the mitral valve must withstand the high pressures in the left ventricle caused by contraction of the left ventricle during ventricular systole, pressures that tend to force a mitral valve prosthesis deployed across a mitral valve annulus into the left atrium.

Additional background art includes US Application No. 2011/0137397 by Chau et al., which discloses "Embodiments of prosthetic valves for implantation within a native mitral valve are provided. A preferred embodiment of a prosthetic valve includes a radially compressible main body and a one-way valve portion. The prosthetic valve further comprises at least one ventricular anchor coupled to the main body and disposed outside of the main body. A space is provided between an outer surface of the main body and the ventricular anchor for receiving a native mitral valve leaflet."

SUMMARY OF THE INVENTION

An aspect of some embodiments of the invention relates to prosthetic heart valve. Optionally, to prosthetic mitral valves. Some embodiments of the invention relate to methods and devices suitable for deploying prosthetic heart valves. Optionally, prosthetic mitral valves.

According to an aspect of some embodiments of the invention, there is provided a method of deploying an expandable prosthetic mitral valve in a subject, the method comprising:

deploying a first component of the prosthetic mitral valve in a left atrium;

deploying a second component of the prosthetic mitral valve in a left ventricle; and approximating the first and the second components so that leaflets of a native mitral valve are trapped between the first and the second components.

In an exemplary embodiment of the invention, approximating comprises approximating by pulling a wire connecting the first and the second elements.

In an exemplary embodiment of the invention, the method further comprises joining said first and second elements to maintain an approximated position.

In an exemplary embodiment of the invention, approximating comprises tightly trapping the native mitral valve leaflets.

In an exemplary embodiment of the invention, the method further comprises piercing said leaflets by at least one of the first or the second components.

In an exemplary embodiment of the invention, the method further comprises piercing tissues surrounding said leaflets by at least one of said first or said second components.

According to an aspect of some embodiments of the invention, there is provided a prosthetic mitral valve suitable for deployment in a mammalian heart, comprising:

a) an annulus part defining a prosthetic mitral valve lumen and having a proximal portion, the annulus part having a deployed configuration configured for deployment inside a left atrium of a heart wherein the proximal portion passes into the mitral valve annulus of the heart; and b) a ventricle part, configured for deployment in a left ventricle of a heart having a deployed configuration configured for at least partially encircling the proximal portion of the annulus part.

According to an aspect of some embodiments of the invention, there is also provided a deployment device for transapically deploying a prosthetic mitral valve contained therein, comprising:

a) a substantially tubular delivery housing including a delivery lumen having an opening at a distal end thereof, the delivery housing configured for transapical entry into a mammalian heart, distal end first;

b) inside the delivery lumen, an annulus part of a prosthetic mitral valve defining a prosthetic mitral valve lumen and having a proximal portion, in a compact delivery configuration, the annulus part outwardly radially expandable subsequent to release from the delivery housing to a deployed configuration configured for deployment inside a left atrium of a heart in which deployed, wherein the proximal portion passes into the mitral valve annulus of the heart;

c) inside the delivery lumen, proximally from the annulus part, a ventricle part of the prosthetic mitral valve physically separate from the annulus part, in a compact delivery configuration, the ventricle part outwardly radially expandable subsequent to release from the delivery housing to a deployed configuration configured for deployment in a left ventricle of a heart at least partially encircling the proximal portion of the annulus part;

d) an annulus-part release component allowing release of the annulus part through the distal end of the delivery housing;

e) a ventricle-part release component allowing release of the ventricle part through the distal end of the delivery housing; and f) a joining component functionally associated with the annulus part and the ventricle part, the joining component configured to bring the annulus part and the ventricle part together when the annulus part is in the deployed configuration subsequent to release from the delivery housing, allowing deployment of the prosthetic mitral valve in a heart.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE FIGURES

Some embodiments of the invention are herein described with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1A:
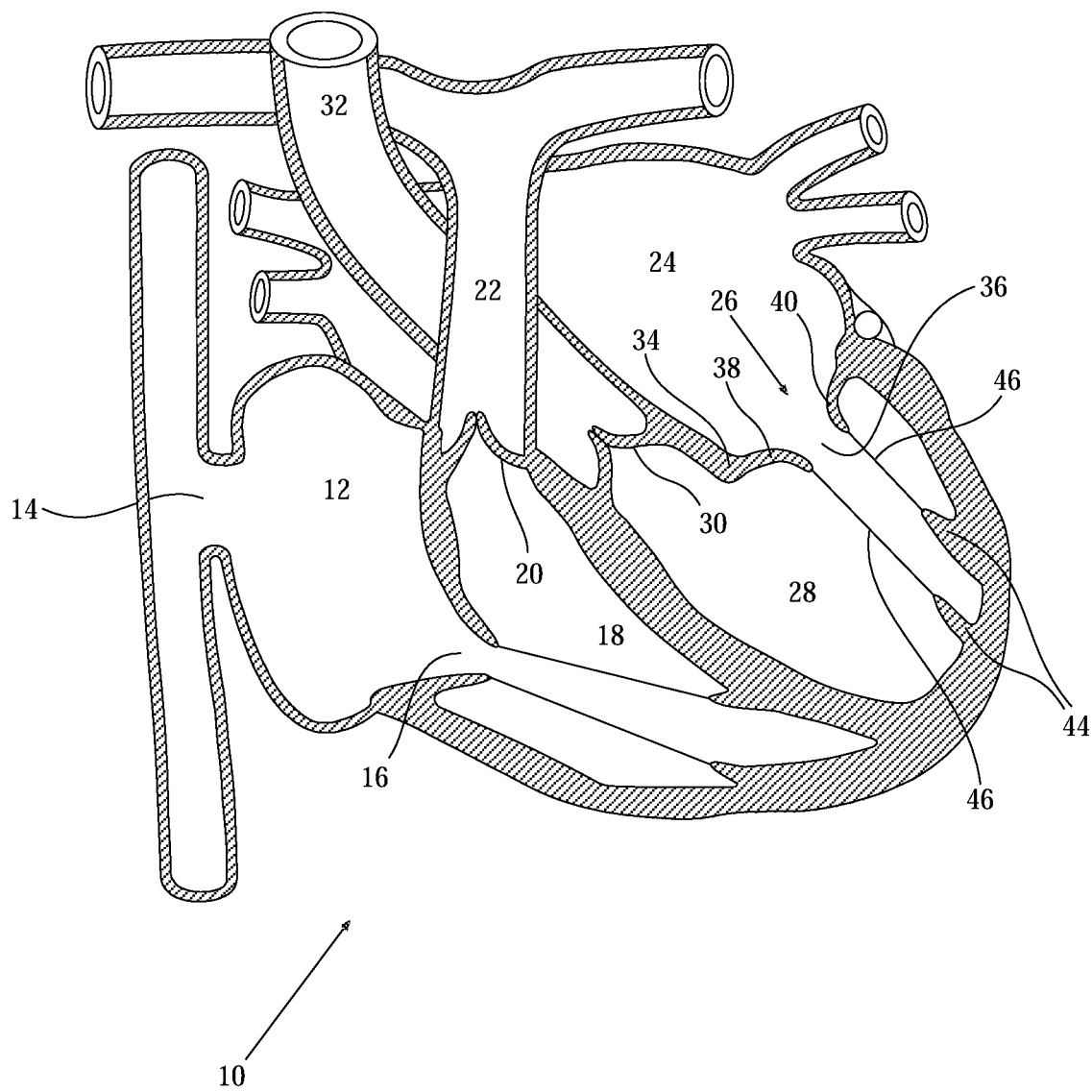
FIGS. 1A and 1B schematically depict a normal adult human heart in cross-sectional long axis view during atrial systole (FIG. 1A) and during ventricular systole (FIG. 1B), to help understand some embodiments of the invention.
Figure 1B:
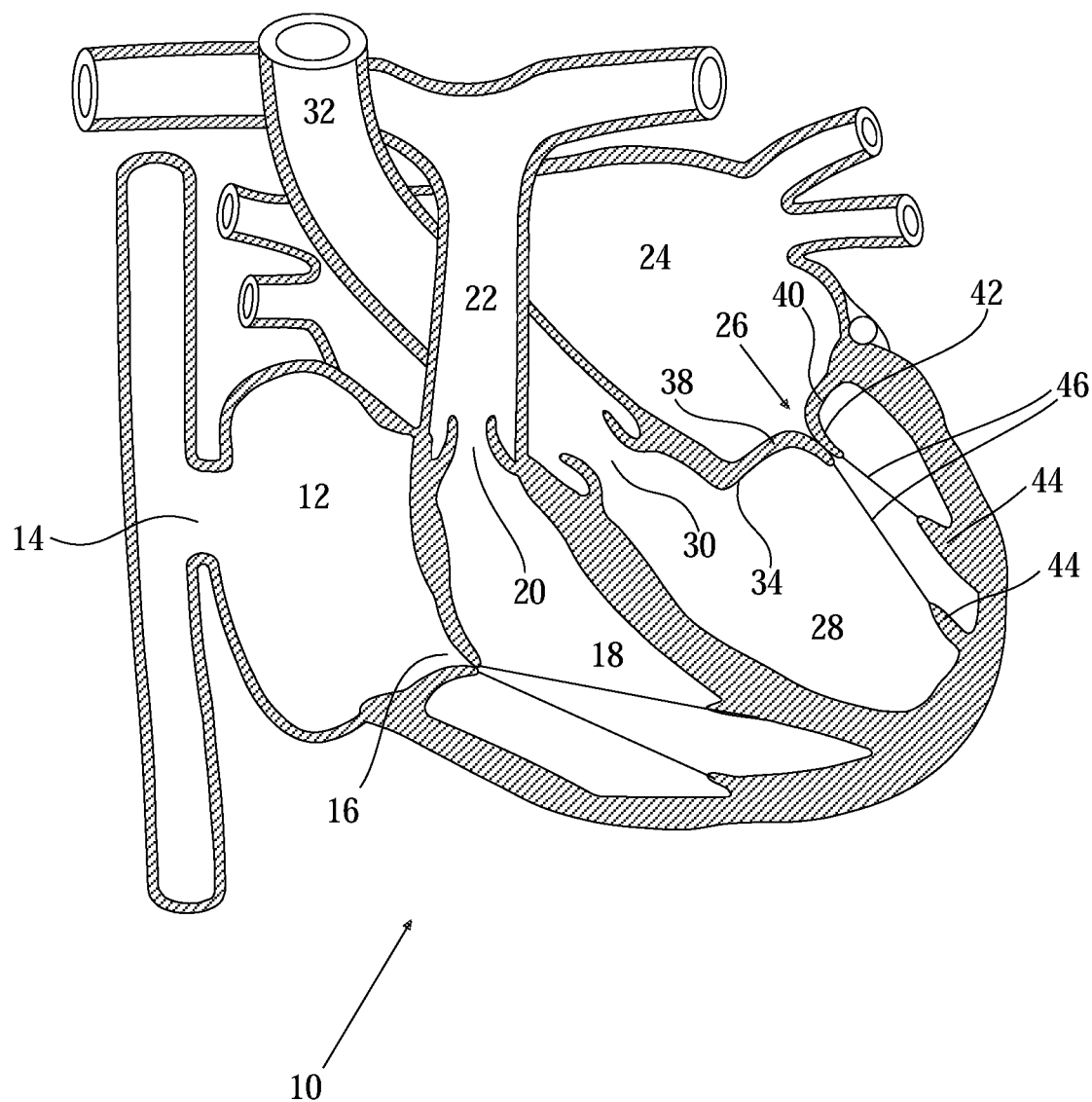

An aspect of some embodiments of the invention relates to prosthetic heart valves. Optionally, to prosthetic mitral valves. Some embodiments of the invention relate to methods and devices suitable for deploying prosthetic heart valves. Optionally, prosthetic mitral valves.

An aspect of some embodiments of the invention relates to a method of deploying a prosthetic mitral valve comprises; deploying a first prosthetic mitral valve portion against the left atrial surface of the mitral valve leaflets, deploying a second prosthetic mitral valve portion inside a left ventricle, and approximating the first and second portions so that the mitral valve leaflets are trapped between the first and second portions. Optionally, at least one wire connected the first and second portions is used to guide the second portion towards the first portion. Alternatively, the wire is used to guide the first portion towards the second portion. Alternatively, the wire is used to close the distance between the first and second portions.

In an exemplary embodiment of the invention, anchoring is performed only to the leaflets, for example, the annular part and the ventricle part are placed on opposite sides of the leaflets and apply force to hold tightly to the leaflets. Alternatively, at least some support is provided by the surrounding tissues, for example, the annulus part extends outwards against the fibrous ring and/or walls of the left atrium. Potentially, the extending outwards of the annulus part prevents or reduces migration of the valve into the left ventricle.

In an exemplary embodiment of the invention, top and bottom portions are joined to one another. Optionally, the joining is performed by elements that bend and/or clasps.

In an exemplary embodiment of the invention, the first and second portion are joined and/or approximated so that the leaflets are clamped hard between the first and second portions. Potentially, the leaflets are clamped hard enough so that migration of the valve into the left atrium (e.g., during systole) is prevented and/or migration into the left ventricle (e.g., during diastole) is prevented. Optionally, the clamping is not hard enough to reduce blood flow to the leaflets to cause necrosis.

Optionally, a tether (e.g., as described below) is used to prevent or reduce migration of the valve.

In an exemplary embodiment of the invention, the pressure applied between the first and second portions to the leaflets is maintained by tension in the wire connecting the first and second portions. Alternatively or additionally, the force is maintained by the attachment elements connecting the first and second portions.

In an exemplary embodiment of the invention, the approximating does not need to be exact, as some tolerance is allowed. Optionally, the second portion is larger than the first portion, so that the second portion surrounds the leaflets and/or the first portion.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

A potential advantage of some embodiments of the invention, is retaining the deployed prosthetic mitral valve, especially during systole, against the generated high pressures in the left ventricle caused by contraction of the left ventricle, without forcing the prosthetic mitral valve into the left atrium.

In an exemplary embodiment of the invention a prosthetic mitral valve comprises two parts, an annulus part (e.g., for deployment in the left atrium) and a ventricle part (e.g., for deployment in the left ventricle).

In an exemplary embodiment of the invention, when deployed, the annulus part is deployed inside a left atrium across the mitral valve annulus (e.g., within the annulus). Optionally, the annulus part is deployed against the atrial aspect of the leaflets. Optionally or additionally, the annulus part is deployed within the native annulus against the leaflets so that the leaflets all or mostly lie inside the left ventricle (e.g., similar leaflet state as during diastole).

In an exemplary embodiment of the invention, the deployment occurs by retracting the expanded annulus part into the native mitral valve annulus. Alternatively, the annulus part is expanded within the native annulus.

In an exemplary embodiment of the invention, a proximal portion of the annulus part is sized and/or positioned so that the annulus part passes into (and in some embodiments through) the mitral valve annulus. Optionally, the proximal portion is sized and/or positioned to extend to about the edge of the native leaflets. Alternatively, the proximal portion is sized and/or positioned to extend past the edge of the native leaflets into the left ventricle.

In an exemplary embodiment of the invention, the ventricle part of the prosthetic mitral valve is deployed inside the left ventricle. Optionally, the ventricle part is displaced towards the mitral valve annulus (e.g., by pulling on the wire connecting the parts) so that the ventricle part at least partially encircles the proximal portion of the annulus part. For example about 360 degrees along the circumference, or about 345 degrees, or about 330 degrees, or about 315 degrees, or about 300 degrees, or about 270 degrees, or other smaller or intermediate dimensions. Potentially, the use of the partially encircling ventricle part does not require cutting the chords, as the partial circumference ventricle part can be positioned even in the presence of the chords. Optionally, the ventricle part is fixed to the proximal portion of the annulus, for example, using anchoring elements, for example, bending elements.

In some embodiments, the ventricle part of the prosthetic mitral valve has a diameter about the same or larger than that of the native mitral valve orifice. For example, the diameter is about 1 mm larger, or about 3 mm, or about 5 mm, or about 7 mm, or about 10 mm, or other smaller, intermediate or larger diameters larger. Potentially, the larger diameter allows easier positioning of the ventricle part around the leaflets and/or annulus part.

In an exemplary embodiment, the ventricle part of the prosthetic mitral valve at least partially encircles the native mitral valve leaflets as well as the proximal portion of the annulus part of the prosthetic mitral valve, thereby trapping the leaflets between the ventricle and the annulus parts. Optionally, both mitral leaflets are encircled. Alternatively, one leaflet is fully encircled and one leaflet is at least partially encircled. Alternatively, one leaflet is at least partially encircled and one leaflet is not. Alternatively, none of the mitral leaflets are encircled, but the portion of the annulus part (e.g., proximal portion) extending into the left ventricle is at least partially encircled or fixed thereto.

Thereby the ventricle part of the prosthetic mitral valve acts substantially as a "locking ring". Potentially, movement of the prosthetic mitral valve into the left atrium is prevented or significantly reduced, even during systole.

Exemplary Method of Treatment

Figure 7:
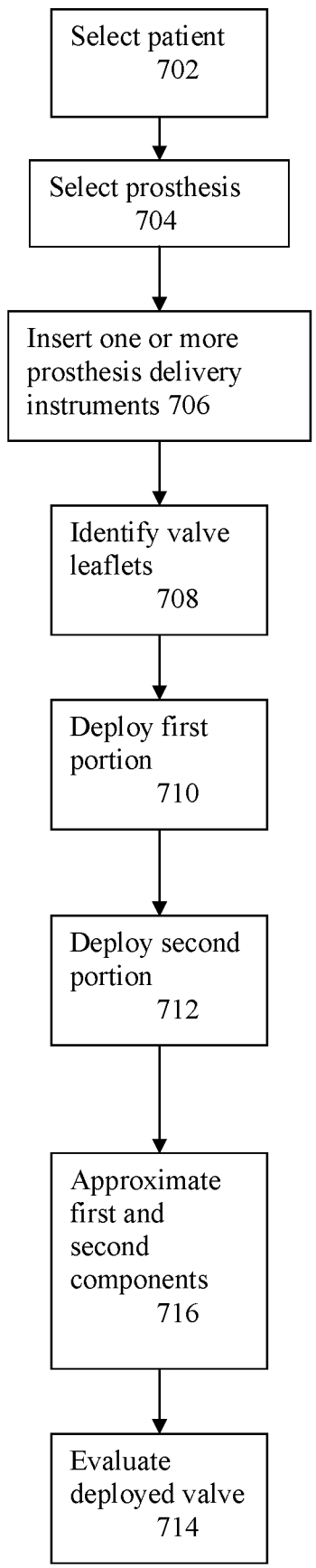
FIG. 7 is flowchart of a method of treating a patient by mitral valve replacement, in accordance with an exemplary embodiment of the invention.

FIG. 7 is a flowchart of a method of treating a patient in accordance with an exemplary embodiment of the invention. It should be noted that the figure is not necessarily limited to the method described below, for example, as some steps are optional and different devices can be used.

Optionally, at 702, a patient is selected for minimally invasive or percutaneous mitral valve replacement, in accordance with an exemplary embodiment of the invention. The patient is selected, for example, by the treating physician. Some not necessarily limiting examples of patient indications include; non-surgical candidates, mitral valve prolapse, mitral valve stenosis, In some embodiments, the heart is not stopped from beating during the procedure, even as the prosthetic valve is deployed. Potentially, patients can be treated that would otherwise be refused surgery. Alternatively, the beating of the heart is stopped for at least part of the duration of the procedure.

Optionally, at 704, a suitable valve prosthesis adapted for anchoring to the leaflets is selected, in accordance with an exemplary embodiment of the invention. Further details about the valve are provided, for example, in the section "Exemplary Prosthetic Mitral Valve".

Optionally, at 706, the prosthetic valve is inserted into the body, in accordance with an exemplary embodiment of the invention. Optionally, a percutaneous approach is used. Optionally, one catheter is inserted into the body to deliver the single component or dual component valve. Alternatively, two catheters are inserted, each catheter delivering one piece of the two piece valve.

Some not necessarily limiting approaches include; femoral vein/jugular vein→right atrium→transseptal (e.g., punctured using a suitable needle or radiofrequency ablation device)→left atrium (→optional left ventricle); femoral artery→aorta→left ventricle (→optional left atrium).

Alternatively or additionally, a minimally invasive approach is used, for example, trans-apical. Alternatively or additionally, the open heart surgery approach is used.

Optionally, the patient is placed under general anesthesia. Alternatively, conscious sedation is used. Alternatively or additionally, local anesthesia is used.

In the case of the trans-apical approach, access to the left ventricular apex of the heart is gained, for example, through a left anterolateral mini-thoractomoy in the fifth intercostal space with horizontal opening of the pericardium and optionally placement of stay sutures for exposure. Optionally, a retractor is placed, exposing the heart apex. Optionally or additionally, two rows of 3-0 polpropylene pledgeted felt purse string sutures are placed around the left ventricular apex creating a 3-4 cm diameter area exposed for access. Optionally or additionally, a 4000 Units of heparin bolus is administered intravenously.

Optionally, at 708, the mitral valve leaflets are identified. Optionally, a TEE (trans-esophageal echo) probe is positioned to observe the left ventricular long axis of the heart throughout the operation. Optionally or additionally, the TEE is used to visualize the chords.

Other not necessarily limiting imaging modalities can be used to identify the leaflets, for example, fluoroscopy.

At 710, the first component of the valve is deployed, in accordance with an exemplary embodiment of the invention. For example, deployment occurs as described with reference to FIG. 8. Optionally, the first component is deployed in the left atrium.

Optionally, at 712, the second component of the valve is deployed, in accordance with an exemplary embodiment of the invention. For example, deployment occurs as described with reference to FIG. 8. Optionally, the second component is deployed in the left ventricle.

Optionally, at 716, the first and second components are approximated. Optionally or additionally, the first and second components are joined together. For example, as described with reference to FIG. 8.

Optionally, at 714, the deployed prosthetic valve is evaluated. Optionally, the location of the valve is evaluated, for example, using one or more imaging modalities such as ultrasound.

Optionally or additionally, the function of the valve is evaluated, for example, using one or more imaging modalities to visualize the blood flow such as Doppler ultrasound.

Exemplary Prosthetic Mitral Valve

Thus, according to an aspect of some embodiments of the invention there is provided a prosthetic mitral valve suitable for deployment in a mammalian heart, comprising:

a) an annulus part, defining a prosthetic mitral valve lumen and having a proximal portion, the annulus part having a deployed configuration configured for deployment inside a left atrium of a heart in which deployed wherein the proximal portion passes into (and in some embodiments, through) the mitral valve annulus; and b) a ventricle part, configured for deployment in a left ventricle of a heart, the ventricle part having a deployed configuration configured for at least partially encircling the proximal portion of the annulus part.

In an exemplary embodiment of the invention, the annulus part and the ventricle part are physically separate components.

In an exemplary embodiment, the ventricle part is sized and/or shaped, in the deployed configuration, to at least partially encircle the native mitral valve leaflets of the heart in which deployed. In some embodiments the native mitral valve leaflets serve as a seal to reduce or prevent blood flow from regurgitating from the left ventricle to the left atrium during systole. Potentially, the bulk and complexity of the prosthetic cardiac valve is reduced, for example, by not requiring additional material to the annulus part to seal the valve against regurgitation of blood.

In an exemplary embodiment, in the deployed configuration the annulus part of the prosthetic mitral valve has a funnel shape, for example, having a narrower (axial dimension) proximal portion and a wider (axial dimension) distal portion. Alternatively, a cylinder shape is used. Optionally, when deployed in a heart, the wider distal portion rests against the inner walls of the left atrium in proximity of the native mitral valve annulus. Alternatively, the wider distal portion does not rest against the left atrium walls, and/or the fibrous ring, but rests only against the leaflets. For example, the distal portion is short or does not extend to the walls. Potentially the prosthetic mitral valve is prevented by the contact with the atrial walls from moving into the left ventricle, for example, during diastole.

In some embodiments, when deployed in a heart, the proximal portion of the annulus passes into the mitral valve annulus, and in some embodiments into the left ventricle, and in some embodiments even past the edges of the native mitral valve leaflets.

In an exemplary embodiment, in the deployed configuration the ventricle part of the prosthetic mitral valve is ring-shaped (a partial or a complete ring). The inner diameter of the ventricle part is sufficient to at least partially encircle the proximal portion of the annulus part, and in some embodiments, at least one of the native mitral valve leaflets of the heart are trapped by the encircling. Optionally, the ventricle part has a relatively small axial dimensions in the deployed configuration so as to have an unobtrusive low profile when deployed inside a left ventricle, potentially not substantially interfering with left ventricle functioning, for example by not partially occluding or causing turbulence in the vicinity of the aortic valve.

Valve Mechanism

In an exemplary embodiment, the annulus part of the prosthetic mitral valve includes a valve mechanism functionally associated with the prosthetic mitral valve lumen, for example, the valve is attached to the annulus part using one or more not necessarily limiting methods including; dip molded thereon, glue, sutures, crimped. Alternatively, the valve mechanism is attached to the ventricle part. Alternatively, the valve mechanism is at least partially attached to the annulus part and at least partially attached to the ventricle part, for example, one or more leaflets on the ventricle part and one or more leaflets on the annular part.

In some embodiments, the valve mechanism is suitable for functioning as a mitral valve even if not originally designed as a mitral valve replacement, that is to say, to prevent flow of blood from the left ventricle to the left atrium through the prosthetic mitral valve lumen during systole but to allow flow of blood from the left atrium to the left ventricle during diastole. The valve mechanism can be any suitable valve mechanism, some not necessarily limiting examples include mechanical valves such as; a bileaflet-mechanism (St. Jude mechanism), a caged-ball mechanism (e.g., Starr-Edwards mechanism), or a tilting-disc mechanism (e.g., Bjork-Shiley mechanism). Alternatively, in some embodiments, the valve mechanism is a biological and/or synthetic leaflet-valve mechanism including at least two leaflets, in some embodiments at least three leaflets. Optionally, valves designed for replacement of valves other than the mitral valve can be used, for example, aortic replacement valves. Not necessarily limiting examples include; Lotus™ or CoreValve™ mentioned above. Optionally, the valve mechanism, for example, the leaflet-valve mechanism, is located inside the prosthetic mitral valve lumen. Optionally, the valve mechanism is positioned within the prosthetic mitral valve lumen of the proximal portion, so that, when deployed, the valve mechanism is located within the native mitral valve annulus and/or inside the left ventricle of a heart in which deployed. Optionally, the position of the valve mechanism is positioned so that the trapped leaflets and the prosthetic valve mechanism acts as a seal to blood.

In some embodiments, the artificial valve mechanism, including leaflet-valve mechanism is configured so as not to be subject to prolapse into a left atrium as can happen with native mitral valve leaflets. In some embodiments where a valve mechanism includes leaflets that are potentially subject to prolapse, the prosthetic mitral valve optionally includes a prolapse-preventing component, for example as described in US 2002/0065554 and US 2004/0138745 or as implemented in the Endovalve™ (Endovalve Inc., Princeton, N.J., USA). Alternatively, where a valve mechanism includes leaflets that are potentially subject to prolapse, the prosthetic mitral valve optionally includes a prolapse-preventing component that is substantially an artificial chorda, for example as described in WO 2009/134701. Alternatively, no prolapse preventing component is used, for example if using a trileaflet valve design such as an aortic replacement valve.

Dynamic Conformation

In some embodiments, the annulus part of the prosthetic mitral valve is configured, (e.g., in the deployed configuration) to dynamically conform to the native mitral valve annulus and/or to the atrial walls in proximity of a native mitral valve of a heart in which deployed. For example, in some such embodiments, the annulus part is self-expanding and dimensioned to be slightly wider (radial dimension) than the native mitral valve annulus and/or atrial walls of the heart in which deployed so that the annulus part is biased to radially expand against the atrial walls and/or the native mitral valve annulus. Potentially, as the heart beats and the shape and/or dimensions of the atrial walls and/or of the native mitral valve annulus change (e.g., expansion and/or compression), the annulus part dynamically conforms, potentially assisting in maintaining a seal between the left atrium and left ventricle and/or allowing substantially natural movement of the heart. Optionally, the valve is made out of an elastic material which allows for the dynamic conformation, for example, Nitinol. Optionally or additionally, the valve is designed with one or more features that allow for expansion and/or contraction, for example, within the struts, one or more 'S', 'Z', or other similar shapes.

Expandable Annulus Part

In some embodiments, the annulus part is outwardly radially expandable from a compact delivery configuration to the deployed configuration. Optionally, the annulus part has a larger outer radius in the deployed configuration than in the delivery configuration, allowing minimally-invasive deployment of the prosthetic mitral valve, for example, transapically, percutaneously, for example with the help of a deployment device such as a delivery catheter or similar.

In some embodiments, the annulus part is expandable from the delivery configuration to the deployed configuration by application of a radially outwards force to an inner surface thereof, for example, with a catheter-mounted balloon that can be expanded and retracted, for example, by the operator outside of the body of the patient injecting fluid into the balloon. In one not necessarily limiting example, the annulus part is made out of a material that can be balloon expanded, for example, stainless steel 316L.

In some embodiments, the annulus part is self-expanding from the delivery configuration to the deployed configuration, for example, upon removal of an encasing sheath. In one not necessarily limiting example, the annulus part is made out of a memory material, for example, Nitinol.

Expandable Ventricle Part

In some embodiments, the ventricle part is outwardly radially expandable from a compact delivery configuration to the deployed configuration.

Optionally, the ventricle part has a larger outer radius in the deployed configuration than in the delivery configuration, allowing minimally-invasive deployment of the prosthetic mitral valve, for example, transapically, percutaneously, for example with the help of a deployment device such as a delivery catheter or similar.

In some such embodiments, the ventricle part is expandable from the delivery configuration to the deployed configuration by application of a radially outwards force to an inner surface thereof, for example, with a catheter-mounted balloon.

In some such embodiments, the ventricle part is self-expanding from the delivery configuration to the deployed configuration. Optionally, the annulus part and/or ventricle part are retractable, for example, by replacing the encasing sheath. Potentially, the valve position is adjustable.

Connecting of the Two Parts

As noted above, in some embodiments the annulus part and the ventricle part of the prosthetic mitral valve are two physically separate components.

In some embodiments, the annulus part and the ventricle part are configured for mutual fixation in the deployed configurations, that is to say, when each part is in a deployed configuration and the prosthetic mitral valve is deployed in a heart, the two parts can be fixed one to the other. Optionally or additionally, the two parts are approximated (e.g., to align the parts) and then attached to one another. In some embodiments, the configuration comprises the presence of eyelets, gaps, tabs or the like allowing mutual fixation, optionally with the help of an additional component, for example, a suture, attachment rings, ties and the like, for example, as will be described below.

In some embodiments, the annulus part and the ventricle part are mateable in the deployed configuration, that is to say, the annulus part includes one or more mating features configured to engage one or more mating features in the ventricle part. In some embodiments, at least one of the annulus part and the ventricle part includes bending mating features, configured to be bent (in this context bent being an adjective, not a verb) when the annulus part and the ventricle part are mated (in this context, mated being an adjective not verb).

Tether

In some embodiments, the prosthetic mitral valve further comprises at least one elongated tether (e.g., a string, a filament, a thread, for example of non-dissolving suture material, polyethylene or PTFE) configured to assist in preventing the deployed prosthetic mitral valve from moving into the left atrium, for example, during systole.

In some embodiments, the prosthetic mitral valve further comprises at least one elongated tether having a distal end functionally associated with the annulus part (e.g., tied, glued, crimped thereto) and a proximal end configured for securing in proximity of the apex of a heart in which deployed, for example, sutured, tied to an anchor. Potentially, the tether maintains the position of the valve under pressure in the annulus part (e.g., when valve is closed during systole) directed from the ventricle to the atrium assisting in preventing the annulus part from moving into the left atrium. In some cases, a force applied to the proximal end of the tether is at least partially transferred by the annulus part to an atrial surface near the mitral valve annulus.

In some embodiments, the prosthetic mitral valve further comprises at least one elongated tether having a distal end functionally associated with the ventricle part (e.g., tied, glued, crimped thereto) and a proximal end configured for securing in proximity of the apex of a heart in which deployed (e.g., sutured, tied to an anchor), wherein a portion of the tether passes through the annulus part (e.g., loops through, slidingly associated with) so that tension (or other force) applied from the proximal end of the tether (e.g., by the securing to the apex) pulls the ventricle part towards the annulus part. Optionally, the force is at least partially transferred by the annulus part to an atrial surface near a native mitral valve annulus in which deployed. Potentially, the tether assists in preventing the annulus part from moving into the left atrium.

Optionally, the same tether is used to anchor the annulus part and the ventricle part. Alternatively, different tethers are used, for example, at least one tether to anchor the annulus part and at least one different tether to anchor the ventricle part.

Any suitable elongated tether may be used, for example, a string, a filament or a thread, for example of non-dissolving suture material, polyethylene or PTFE.

Optionally, the distal end of a tether is secured (for example, by tying or fastening) to the part of the prosthetic mitral valve to be functionally associated therewith.

Optionally, the distal end of a tether is configured for securing in proximity of the apex of a heart in which deployed by being securable to an anchor penetrating into the cardiac muscle (for example, as disclosed in PCT patent publication WO2007/135101) or by being configured to pass through the cardiac muscle to be secured to a pad that contacts the outer surface of the heart, e.g., such as pads commercially-available with the Coapsys® device from Myocor, Inc., Maple Grove, Minn., USA.

Delivery Device for a Prosthetic Mitral Valve

Embodiments of the prosthetic mitral valve disclosed herein may be deployed using any suitable method, including open-heart surgery and minimally-invasive surgery, for example with a deployment device such as a flexible catheter that enters the left ventricle through the vasculature and the aorta, with a deployment device such as a catheter that enters the left atrium through the roof of the left atrium or transeptally from the right atrium, and/or transapically with a deployment device such as a transapical catheter that enters the left ventricle through the cardiac apex.

In an exemplary embodiment of the invention, the prosthetic mitral valve is transapically deployed using a deployment device, for example, as described herein.

According to an aspect of some embodiments of the invention there is provided a deployment device for transapically deploying a prosthetic mitral valve contained therein, comprising:

a) a substantially tubular delivery housing including a delivery lumen having an opening at a distal end thereof, the delivery housing configured for transapical entry into a mammalian heart the distal end first;

b) inside the delivery lumen, an annulus part of a prosthetic mitral valve (substantially as described above) defining a prosthetic mitral valve lumen and having a proximal portion, in a compact delivery configuration, the annulus part outwardly radially expandable, subsequent to release from the delivery housing, to a deployed configuration configured for deployment inside a left atrium of a heart in which deployed wherein the proximal portion passes into (and in some embodiments through) the mitral valve annulus of the heart;

c) inside the delivery lumen, proximally from the annulus part, a ventricle part of a prosthetic mitral valve (substantially as described above) physically separate from the annulus part, in a compact delivery configuration, the ventricle part outwardly radially expandable, subsequent to release from the delivery housing, to a deployed configuration configured for deployment in a left ventricle of a heart at least partially encircling the proximal portion of the annulus part;

d) an annulus-part release component (in some embodiments, activatable from a proximal end of the delivery housing) allowing release of the annulus part through the distal end of the delivery housing;

e) a ventricle-part release component (in some embodiments, activatable from a proximal end of the delivery housing) allowing release of the ventricle part through the distal end of the delivery housing; and f) a joining component functionally associated with the annulus part and the ventricle part of the prosthetic mitral valve, the joining component configured to bring the annulus part and the ventricle part together when the annulus part is in the deployed configuration subsequent to release from the delivery housing, allowing deployment of the prosthetic mitral valve in a heart.

In some embodiments, the annulus part includes a valve mechanism functionally associated with the prosthetic mitral valve lumen, the valve mechanism suitable for functioning as a mitral valve.

Balloon-Expandable Annulus Part

In some embodiments, the deployment device further comprises an annulus-part expansion assembly, configured to apply a radially outwards force to an inner surface of the annulus part subsequent to release from the delivery housing to radially expand the annulus part from the delivery configuration to the deployed configuration, for example, the annulus-part expansion assembly includes a catheter-mounted balloon catheter.

In some such embodiments, the annulus part and the annulus-part expansion assembly are together configured so that in the deployed configuration, the annulus part conforms to an atrial contour near a native mitral valve in which deployed, for example, when the annulus-part expansion assembly is a catheter-mounted balloon, the balloon has an inflated shape similar to the atrial contour near the native mitral valve, and/or the balloon is a compliant balloon that adopts the shape of the atrial contour near the native mitral valve when inflated. Alternatively or additionally, the balloon is shaped according to the desired deployment shape of the annulus part, for example, having the funnel shape as previously described.

Self-Expanding Annulus Part

In some embodiments, the annulus part is self-expanding from the delivery configuration to the deployed configuration subsequent to release from the delivery housing. In some such embodiments, the annulus part is configured so that in the deployed configuration, the annulus part dynamically conforms to a mitral valve annulus and/or to atrial walls in proximity of the mitral valve of a heart in which deployed, as described above.

Balloon-Expandable Ventricle Part

In some embodiments, the deployment device further comprises a ventricle-part expansion assembly, configured to apply a radially outwards force to an inner surface of the ventricle part subsequent to release from the delivery housing to radially expand the ventricle part from the delivery configuration to the deployed configuration, for example, the ventricle-part expansion assembly includes a catheter-mounted balloon catheter.

Self-Expanding Ventricle Part

In some embodiments, the ventricle part is self-expanding from the delivery configuration to the deployed configuration subsequent to release from the delivery housing.

Tether

In some embodiments, the deployment device further comprises, inside the delivery lumen, at least one elongated tether of a prosthetic mitral valve (as described above), the at least one elongated tether having a distal end functionally associated with the annulus part of the prosthetic mitral valve and a proximal end configured for securing in proximity of the apex of a heart in which deployed, so that a force applied to the proximal end of the tether is at least partially transferred by the annulus part to an atrial surface near a native mitral valve annulus in which deployed.

In some embodiments, the deployment device further comprises, inside the delivery lumen, at least one elongated tether of a prosthetic mitral valve (as described above), the at least one elongated tether having a distal end functionally associated with the ventricle part of the prosthetic mitral valve and a proximal end configured for securing in proximity of the apex of a heart in which deployed, wherein a portion of the tether passes through the annulus part of the prosthetic mitral valve so that force applied to the proximal end of the tether pulls the ventricle part towards the annulus part, and is at least partially transferred by the annulus part to an atrial surface near a native mitral valve annulus in which deployed.

Annulus Part Placement Component

In some embodiments, the deployment device further comprises an annulus-part placement component functionally associated with the annulus part of the prosthetic mitral valve, configured to assist in properly positioning the annulus part in a native mitral valve annulus when in the deployed configuration. In some embodiments, the annulus-part placement component is functional to pull and/or push the annulus part proximally from the volume of the left ventricle (in which the annulus part was expanded to the deployed configuration) into the mitral valve annulus. In some embodiments, the annulus-part placement component is an elongated component, rigid (e.g., a rigid wire) or flexible (e.g., a filament, string or thread), having a distal functionally associated with (e.g., secured, temporarily or permanently) the annulus part and a proximal end that is accessible from the proximal end of the delivery housing, e.g. for pulling or pushing.

In some embodiments, the annulus-part placement component is configured to also function as a deployable tether, substantially as described above.

Mater Component

As discussed above, in some embodiments, the annulus part and the ventricle part are configured for mutual fixation in the deployed configurations.

In some such embodiments, the annulus part and the ventricle part are mateable in the deployed configurations. Optionally, the annulus part includes a first mating feature configured to engage a second mating feature in the ventricle part. Optionally, the deployment device further comprises a mater component, configured to assist in effecting the mating of the annulus part and the ventricle part. In some embodiments, the role of the mater is performed by a joining component, discussed below.

In some such embodiments, at least one of the annulus part and the ventricle part include a bending mating feature, configured to be bent when the annulus part and the ventricle part are mated (as discussed above). Optionally, the mater component is configured to bend the bending mating features. In some embodiments, the role of the mater is performed by a joining component, discussed below.

Joining Component

As noted above, in some embodiments, the deployment device comprises a joining component functionally associated with the annulus part of the prosthetic mitral valve and/or with the ventricle part of the prosthetic mitral valve, the joining component configured to bring the annulus part and the ventricle part together when the annulus part is in the deployed configuration. In an exemplary embodiment of the invention, the joining component is configured to perform one or more functions including:
- to function as a ventricle-part release component, e.g., functional for removing (e.g., by pulling) the ventricle part out of the delivery housing through the distal opening of the delivery housing.
- to function as an annulus-part placement component, e.g., functional for pulling the annulus component into a native mitral valve annulus, substantially as described above.
- to function as a deployable tether, substantially as described above.
- to function as a mater component, substantially as described above, for example, configured to bend mating features of at least one of the annulus part and the ventricle part, thereby mating the two parts.

In some embodiments, the joining component comprises at least one elongated flexible component that is slidingly associated with (e.g., loops around) a portion of the annulus part. Optionally, a proximal end is accessible from a proximal end of the delivery housing (e.g., for pulling), and a distal end secured to the ventricle part. Any suitable elongated flexible component may be used, for example, a string, a filament or a thread, for example of non-dissolving suture material, polyethylene or PTFE. Optionally, the distal end of the joining component is secured (for example, by tying or fastening) to the ventricle part.

In some such embodiments, the joining component is releasably secured to the ventricle part, for example, the joining component is released from the ventricle part after deployment. In some such embodiments, the joining component is fixedly secured (e.g., permanent) to the ventricle part, for example allowing the joining component to serve as a tether.

Figures 2A, 2C:
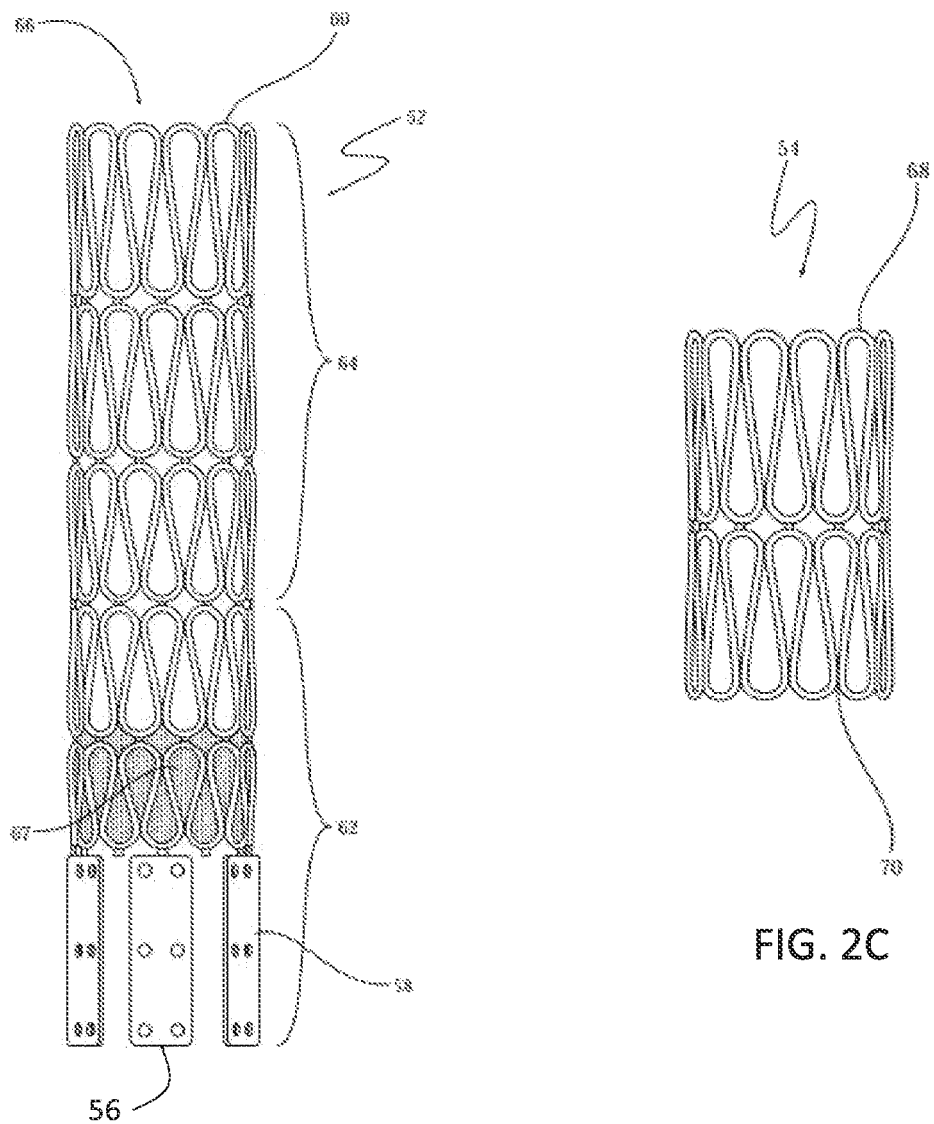
FIGS. 2A and 2C depict the annulus part and the ventricle part of an embodiment of a prosthetic mitral valve as described herein, in a compact delivery configuration, in accordance with an exemplary embodiment of the invention.
Figure 2B:
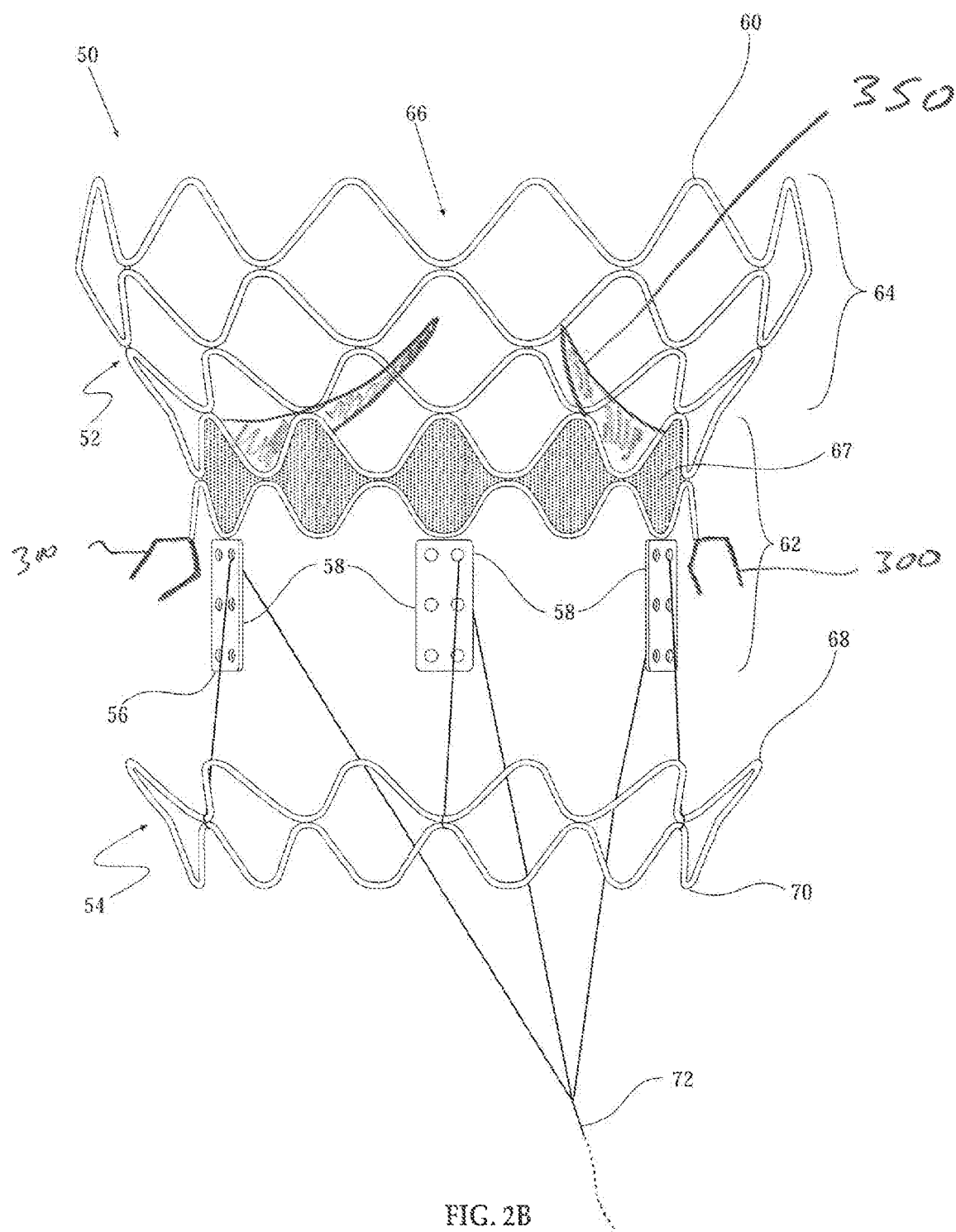
FIG. 2B depicts the annulus part and the ventricle part of the prosthetic mitral valve of FIGS. 2A and 2C, in a deployed configuration, in accordance with an exemplary embodiment of the invention.

Parts of an embodiment of a prosthetic mitral valve as described herein, prosthetic mitral valve 50, are schematically depicted in FIGS. 2A, 2B, and 2C, in accordance with an exemplary embodiment of the invention. In FIGS. 2A, 2B, and 2C, an annulus part 52 and a ventricle part 54 are depicted. Optionally, parts 52 and 54 are physically separate and distinct. Optionally, parts 52 and/or 54 are fashioned of self-expanding material, for example, nitinol. Optionally, parts 52 and/or 54 are biased to a larger outer radius deployed configuration. In one example, parts 52 and/or 54 are substantially self-expanding stents, laser-cut from a 10 mm outer diameter 1 mm thick tube of nitinol.

In an exemplary embodiment of the invention, annular portion 52 comprises a valve mechanism 350, for example, as described in the section "valve mechanism".

In FIGS. 2A and 2C, annulus part 52 and ventricle part 54 are depicted in a compact delivery configuration, for example, as if held inside a delivery lumen of a delivery housing (e.g., of a deployment device such as a valve-deployment catheter), The length of annulus part 52 is, for example, about 20 mm long, or about 24 mm, or about 26 mm, or about 30 mm, or about 34 mm, or about 38 mm, or about 42 mm, or about 46 mm, or about 50 mm, or other smaller, intermediate or longer length. The length of ventricle part 54 is, for example, about 6 mm long, or about 8 mm, or about 10 mm, or about 12 mm, or about 14 mm, or about 16 mm, or about 20 mm, or other smaller, intermediate or larger sizes.

Annulus part 52 defines a prosthetic mitral valve lumen 66 that passes through annulus part 52 between a proximal end 56 and a distal end 60.

Optionally, annulus part 52 is divided into two portions between proximal end 56 and distal end 60, a proximal portion 62 and a distal portion 64. Optionally, distal portion 64 is entirely defined by struts. Optionally or additionally, the distal part of proximal portion 62 is defined by struts while the proximal part is optionally defined by one or more attachment elements adapted to connect to the ventricle part. For example, 1, 3, 5, or other number of attachment elements. For example, perforated tabs 58. The length of tabs 58 is, for example, about 10 mm, about 7 mm, about 5 mm, or other smaller, intermediate or larger lengths. Optionally, the attachment elements are spread around the circumference, for example, about evenly around.

Amongst other functions, tabs 58 constitute configuration of annulus part 52 for mutual fixation of annulus part 52 and ventricle part 54. Other not necessarily limiting examples of attachment elements include; eyelets, gaps, latches.

In some embodiments, attachment elements 300 are adapted for directly grabbing or attaching annulus part 52 to ventricle part 54. Optionally, elements 300 are located on annulus part 52. Alternatively or additionally, elements 300 are located on ventricle part 54. Optionally, attachment elements 300 are finger like extensions oriented so that when ventricle part 54 is approximated with atrial part 52, struts of ventricle part 54 are positioned between the fingers of attachment elements 300. Optionally, elements 300 are bendable, for example, by using a device such as a surgical clamp, fingers of elements 300 can be bent around struts of ventricle part 54 to maintain the approximated position. Alternatively or additionally, elements 300 are one way clasps, so that once struts of ventricle part 54 enter the claps, the struts cannot leave.

In an exemplary embodiment of the invention, disposed inside lumen 66 is a pericardial trileaflet valve mechanism 67. Optionally, valve 67 is secured to the struts making up the distal part of proximal portion 62.

Ventricle part 54 has a distal end 68 and a proximal end 70.

In FIG. 2B, annulus part 52 and ventricle part 54 are depicted unconstrained and adopting a deployed configuration, in accordance with an exemplary embodiment of the invention.

In an exemplary embodiment of the invention, annulus portion (e.g., in the expanded state) has a funnel-like shape (e.g., having a narrower (axial dimension) proximal portion and a wider (axial dimension) distal portion). Alternatively, a cylindrical shape, or other shapes are used. An outer diameter at distal end 60 is, for example, about 30 mm, or about 34 mm, or about 38 mm, or about 42 mm, or about 48 mm, or about 52 mm, or other smaller, intermediate or larger diameters. The outer diameter at proximal end 56 is, for example, about 19 mm, or about 23 mm, or about 27 mm, or about 31 mm, or about 35 mm, or other smaller, intermediate or larger sizes. The total length of annulus part 52 is, for example, about 20 mm, or about 24 mm, or about 28 mm, or about 32 mm, or other smaller, intermediate or larger lengths. Optionally, the length of proximal portion 62 (comprising the replacement leaflets) is, for example, about 10 mm, or about 14 mm, or about 18 mm, or other smaller, intermediate or larger lengths. Optionally, the length of portion 62 includes an additional length of tabs 58 (the tabs described below). Alternatively, the overall length already includes the tabs 58. Alternatively, the tabs 58 do not extend part end of portion 62, for example, incorporated therein.

In some embodiments, the size and/or shape of annulus part 52 is such that annulus part 52 is configured for deployment inside a left atrium of a heart wherein proximal portion 62 passes into a mitral valve annulus and tabs 58 extend into the left ventricle of the heart and at least partially beyond the native mitral valve leaflets, while the outer surface of distal portion 64 snugly rests against the inner walls of the left atrium in proximity of the mitral valve annulus.

In an exemplary embodiment of the invention, the cross section of ventricle part 54 is approximately trapezoidal, potentially the shape around the native leaflets. Alternatively, other shapes are used, for example, circles, ellipses. In some embodiments, the ventricle part 54 of the prosthetic mitral valve has a diameter larger than that of the native mitral valve orifice. Alternatively, the diameter is smaller than the native mitral valve orifice. The outer diameter at distal end 68 and/or proximal end 70 is, for example, about 24 mm, about 28 mm, about 32 mm, or about 36 mm, or about 40 mm, or about 44 mm, or other smaller, intermediate or larger sizes. Optionally, the diameters of ends 68 and 70 are different, to create a tapered or cone-like configuration. The length of portion 206 is, for example, about 6 mm, or about 10 mm, or about 14 mm, or other smaller, intermediate or larger sizes.

In an exemplary embodiment, the size and/or shape of ventricle part 54 is such that when annulus part 52 is deployed inside a left atrium of a heart as described above, ventricle part 54 can be placed over so as to encircle proximal portion 62 of annulus part 52 and the native mitral valve leaflets of the heart.

In an exemplary embodiment of the invention, the valve is designed to fit within a wide range of mitral valve annulus diameters, for example, children, patients with dilated ventricles and/or atria, patients having undergone previous mitral valve surgery and/or cardiac reconstructive surgery.

As noted above, pericardial trileaflet valve mechanism 67 is disposed inside lumen 66 and is secured to the struts making up proximal portion 62 of annulus part 52, for example, valve 67 is sewed, glued, crimped and/or dip-molded onto annulus part 52. Valve mechanism 67 is oriented in a direction so that when annulus part 52 is in a deployed configuration as depicted in FIG. 2B, valve mechanism 67 is functional for allowing the flow of blood from distal end 60 to proximal end 56 through lumen 66. Optionally or additionally, valve 67 is oriented for blocking the retrograde flow of blood from proximal end 56 to distal end 60 through lumen 66. In such a way, valve mechanism 67 is functionally associated with lumen 66 in a manner suitable for functioning as a mitral valve.

In an exemplary embodiment of the invention, the diameter of annulus portion 52 housing replacement valve 67 is, for example, about 12 mm, about 14 mm, about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, or other smaller, intermediate or larger diameters. In some embodiments, a variety of sizes are available for different patient groups. Some not necessarily limiting examples of factors affecting the selection of the size include; age of patient (e.g., pediatric vs adult), mitral valve annulus size (e.g., normal vs dilated, native valve vs prosthetic valve or annuloplasty). Alternatively, only a small number of sizes are available, for example, one size is available for adults regardless of the mitral valve annulus size, as the amount of leaflets squeezed is varied to fit in the different annulus sizes. For example, in a patient with a larger annulus, less leaflet area is squeezed than in a patient with a smaller annulus.

In an exemplary embodiment of the invention, a height of part 52 is long enough to attach to valve 67. Optionally or additionally, the height is long enough to provide anchoring against the leaflets. The height is, for example, at least 5 mm, or at least 7 mm, or at least 10 mm, or at least 15 mm, or at least 20 mm, or other smaller, intermediate or larger values are used.

In an exemplary embodiment of the invention, proximal portion 62 of portion 204 is long enough to pass into the ventricle when deployed in the mitral valve annulus, for example, tabs 58 extend into the ventricle. Alternatively, portion 62 does not extend past the annulus into the ventricle.

In FIG. 2B is also depicted one or more filaments 72 that are configured to act as a joining component to bring annulus part 52 and ventricle part 54 together when in a deployed configuration. Optionally, the distal ends of filament 72 are secured (e.g., by tying, gluing, crimping) to struts of ventricle part 54. Optionally, filament 72 loops around a portion of annulus part 54 (e.g., through perforations in tabs 58, around and/or through struts). Operation of filament 72 as a joining component is discussed in detail hereinbelow.

Figure 3:
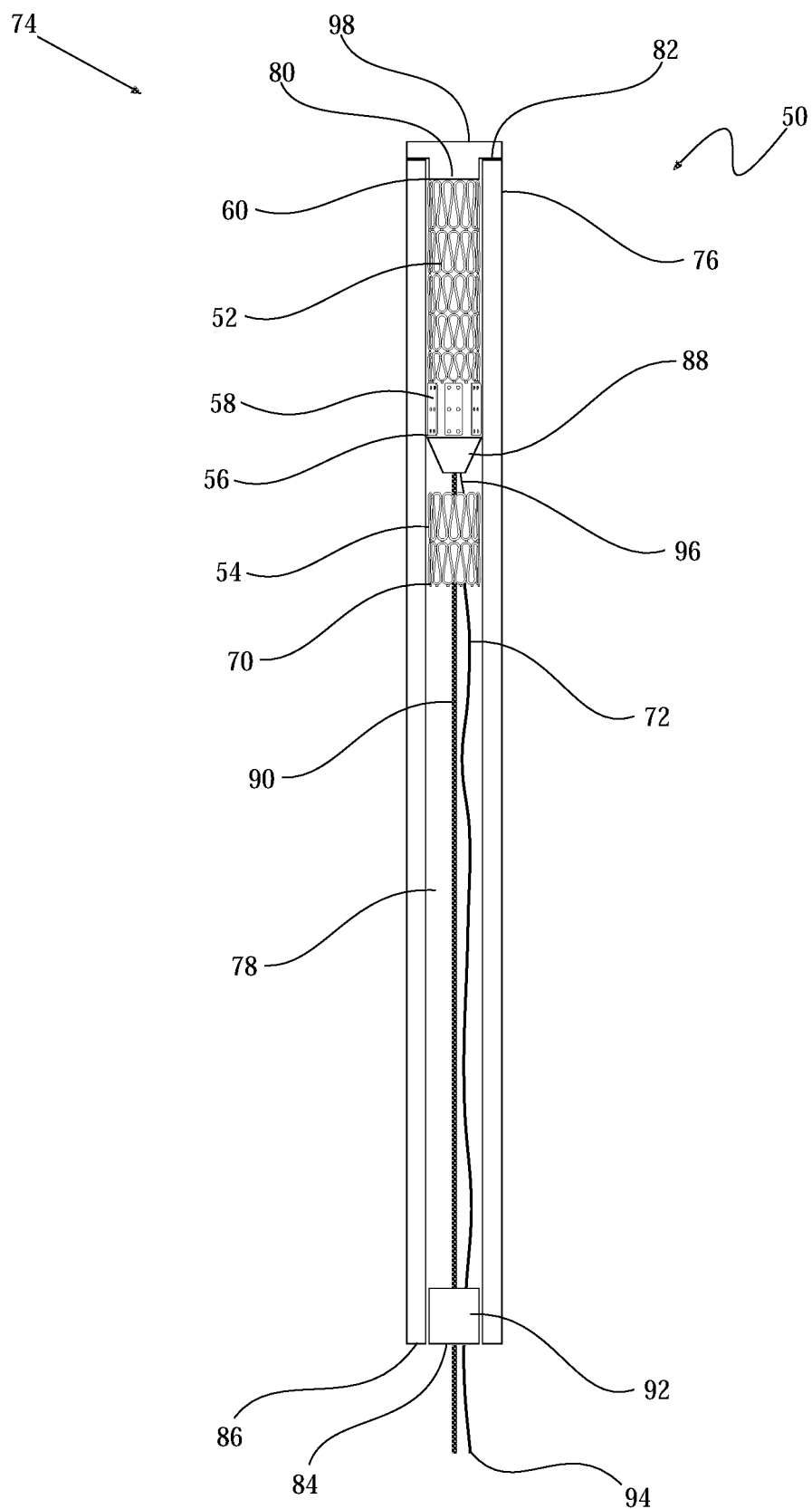
FIG. 3 schematically depicts an embodiment of a deployment device useful for deploying a prosthetic mitral valve of FIGS. 2A, 2B, and 2C in side cross section, in accordance with an exemplary embodiment of the invention.

In FIG. 3, an embodiment of a deployment device, 74, for deploying a prosthetic mitral valve 50 contained therein is schematically depicted in side cross section, in accordance with an exemplary embodiment of the invention. Device 74 is designed for deployment of the valve by placement of the device in the left ventricle, for example, using a transapical approach, or a vascular approach via the aorta. Optionally, deployment device 74 comprises a substantially tubular delivery housing 76. Optionally, device 74 includes a delivery lumen 78 having a distal opening 80 at a distal end 82 thereof. Optionally or additionally, device 74 includes a proximal opening 84 at a proximal end 86 thereof. In some embodiments, Delivery housing 76 is fashioned of biocompatible materials and in a manner known in the art to allow minimally invasive (e.g., transapical or percutaneous) entry into a human heart distal end 82 first.

In an exemplary embodiment, annulus part 52 of prosthetic mitral valve 50 is held inside delivery lumen 78 in a compact delivery configuration, optionally, near distal opening 80.

Optionally, contacting the proximal ends (e.g., tabs 58) of annulus part 52 is a distal end 88 of an optional push rod 90. Optionally, push rod 90 extends proximally, exiting delivery lumen 78 from proximal opening 84 through an optional first passage in an optional sterility preserving sealing ring 92. As is discussed below, push rod 90 constitutes an annulus-part release component that is optionally activatable from proximal end 86 of delivery housing 76, for example, by slidingly pushing push rod 90 in a distal direction. Optionally, push rod 90 is manually activated, for example, by the operator. Alternatively, push rod 90 is automatically activated, for example, by a robot.

Optionally or additionally, a ventricle part 54 of prosthetic mitral valve 50 is held inside delivery lumen 78 in a compact delivery configuration, optionally, proximally to distal end 88 of push rod 90 and optionally surrounding push rod 90.

In some embodiments, annulus 52 and ventricle 54 are physically separate and housed in one tube. Alternatively, two separate delivery tubes are used, one housing annulus 52 and one housing ventricle 54.

In some embodiments, the delivery device is sold pre-assembled and loaded with the selected prosthetic valve. Alternatively, the delivery device is assembled by the physician before the procedure, for example, the delivery device is standard, and the valve is variable. In such a case, the physician may fill the lumen with fluid (e.g., saline) before delivery.

In some embodiments, an optional filament 72 is also held inside delivery lumen 78. For clarity, and as noted above, details of filament 72 will be discussed with reference to FIG. 2B.

Optionally, a proximal end 94 (FIG. 3) of filament 72 comprises a single strand, for example, made of flexible ultrahigh molecular weight polyethylene (UHMWPE). Optionally, proximal end 94 of filament 72 extends proximally, exiting delivery lumen 78 from proximal opening 84 through an optional second passage in optional sterility preserving sealing ring 92.

Optionally, near a distal end 96 (and as seen in FIG. 2B), filament 72 comprises, for example, two, three, five or other number of (e.g., separate) strands (e.g., of UHMWPE) attached (e.g., tied, glued, crimped) to the proximal strand (e.g., single strand). Each one of the separate strands loops around a portion of annulus part 52 (for example, through a perforation in a tab 58) so that the separate strands can slidingly move therethrough. Optionally, one or more of the separate strands are secured (e.g. by tying, gluing, crimping) around an element (e.g., strut) and through a gap in the side of ventricle part 54 so that the strands are distributed (e.g., equally) around the periphery of ventricle part 54.

In some embodiments, filament 72 and tabs 58 together constitute parts of a ventricle-part release component. Optionally, the ventricle release component is activatable (e.g., by the user), for example, from proximal end 86 of delivery housing 76. Optionally or additionally, filament 72 and tabs 58 constitute parts of a joining component configured to bring annulus part 52 and ventricle part 54 together, for example, when annulus part 52 is in a deployed configuration, for example, subsequent to release from delivery housing 76.

Optionally or additionally, filament 72 and tabs 58 constitute parts of an annulus-part placement component configured to assist in properly positioning annulus part 52 in a native mitral valve annulus, for example, when in a deployed configuration. Optionally or additionally, the parts constitute parts of a deployable tether, for example, as described herein.

In some embodiments, the empty volume of delivery lumen 78 is filled with a sterile preservative solution (e.g., glutaraldehyde solution) to maintain the valve mechanism of prosthetic mitral valve 50 sterile and ready for use.

Optionally, a cap 98 seals distal opening 80, potentially preventing or reducing loss of the preservative solution and of sterile conditions inside delivery lumen 78.

Exemplary Deployment Method

Figure 5A:
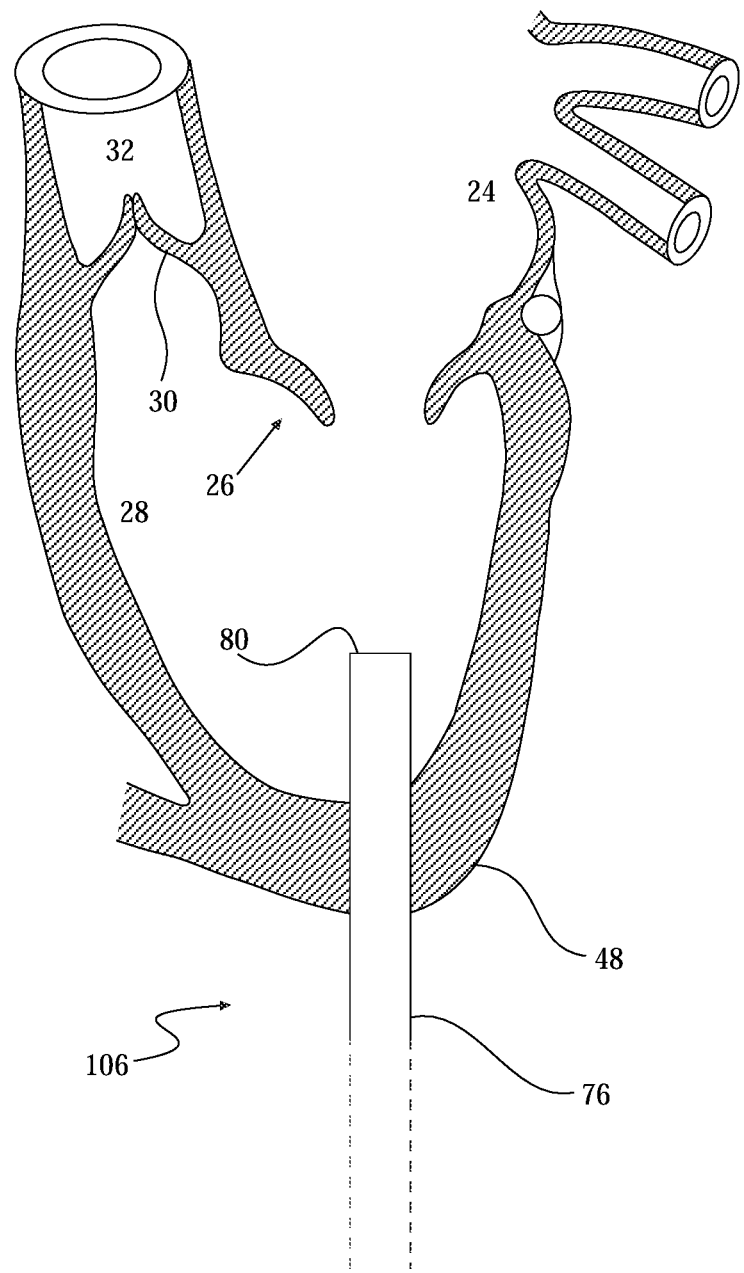
FIGS. 5A-5G depict the deployment of an additional embodiment of a prosthetic mitral valve, in accordance with some embodiments of the invention.
Figure 5B:
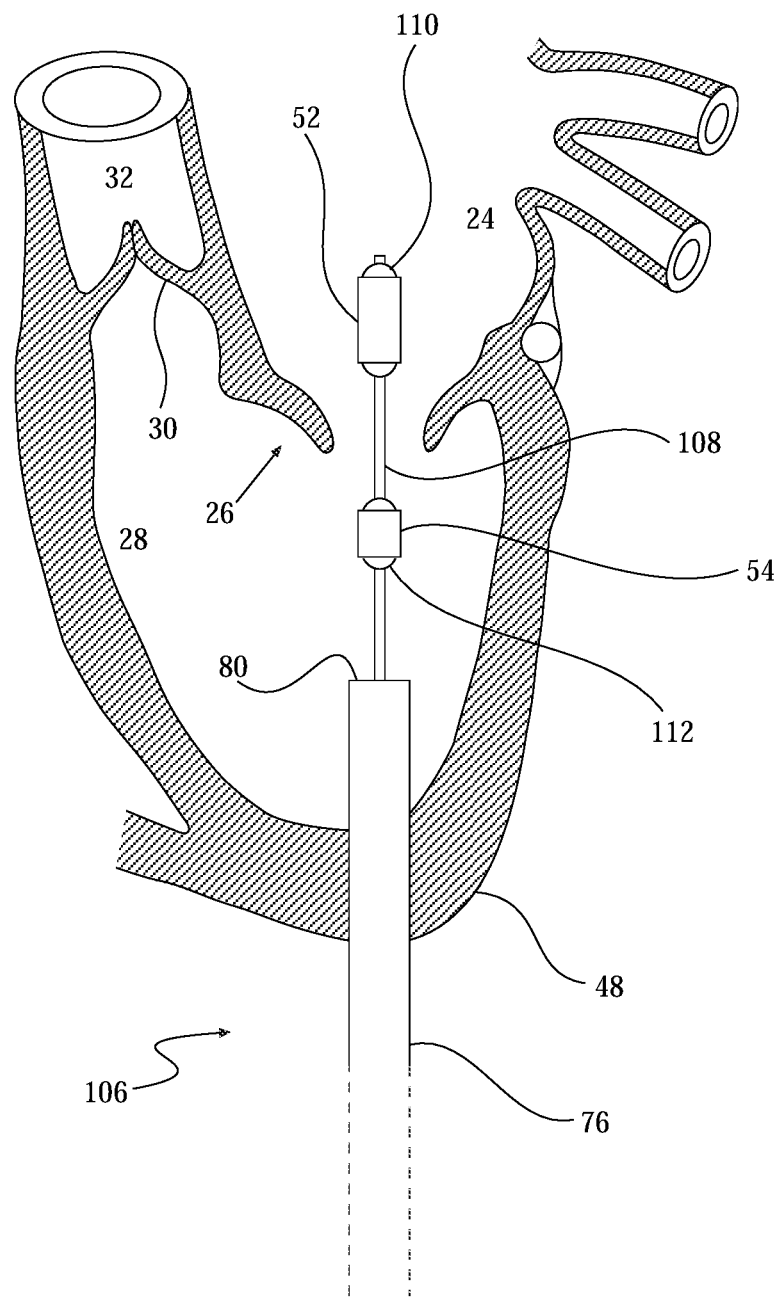
Figure 5C:
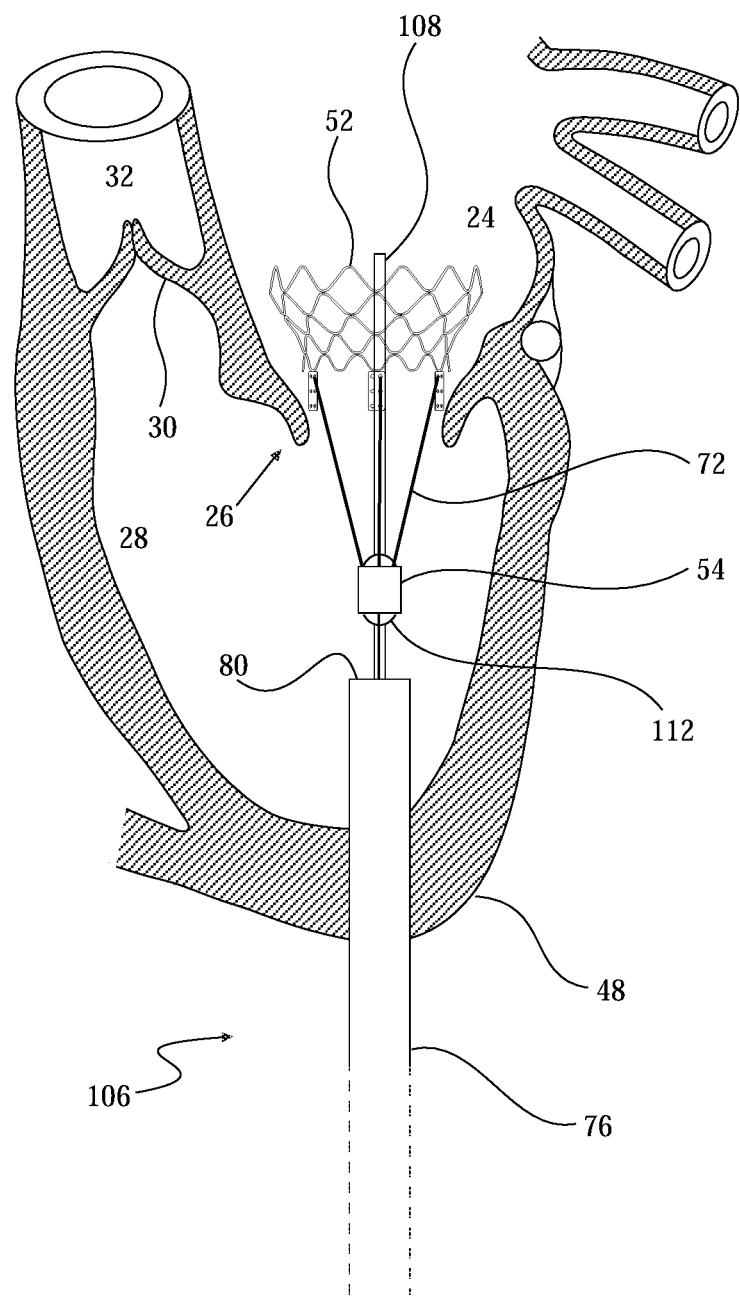
Figure 5D:
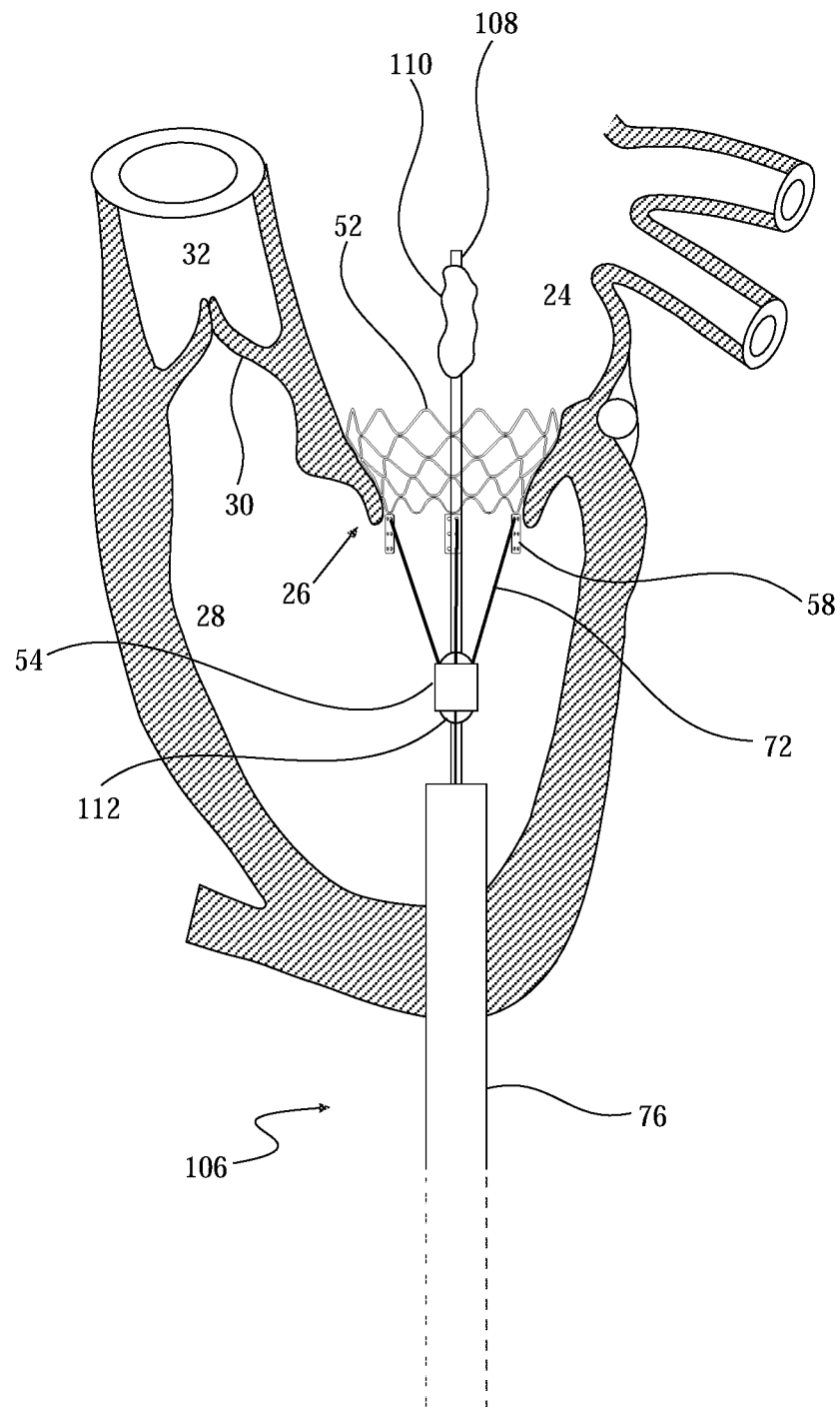
Figure 5E:
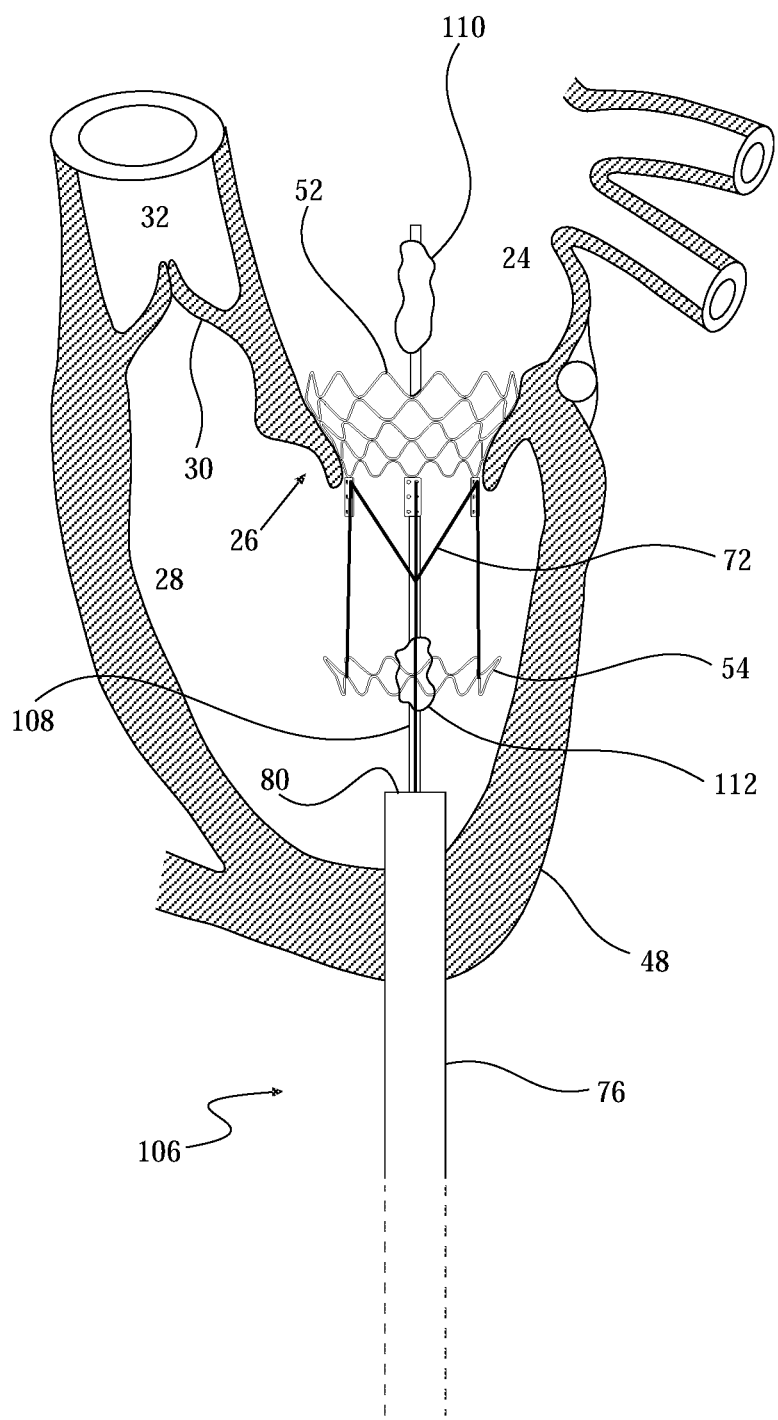
Figure 5F:
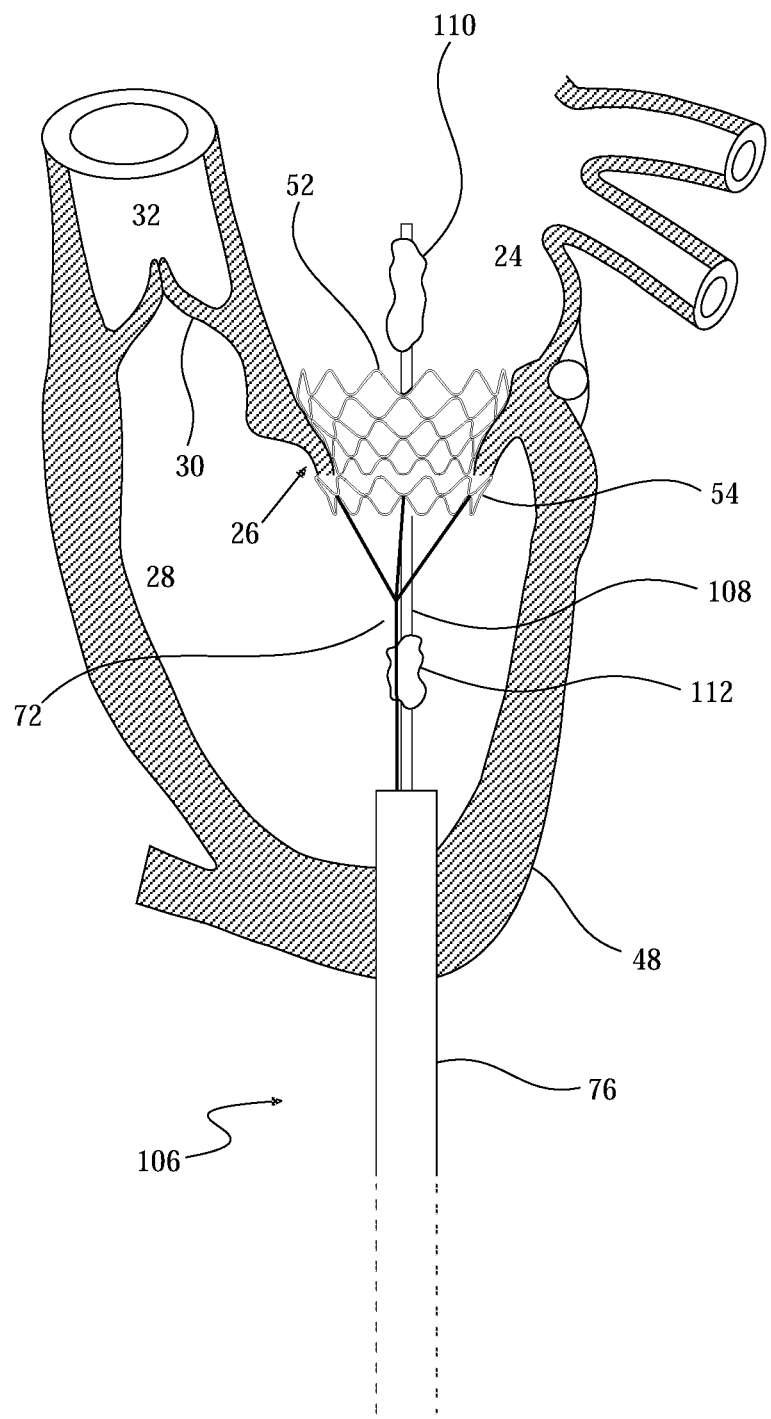
Figure 5G:
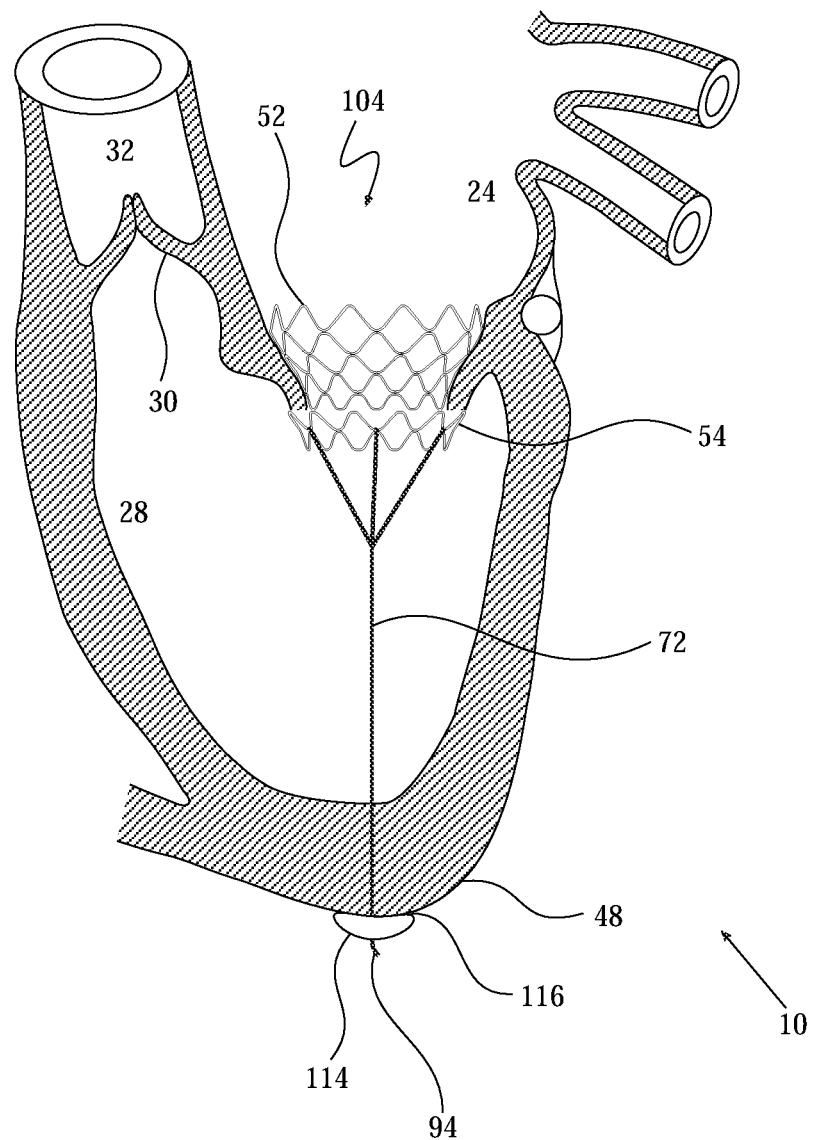
Figure 6:
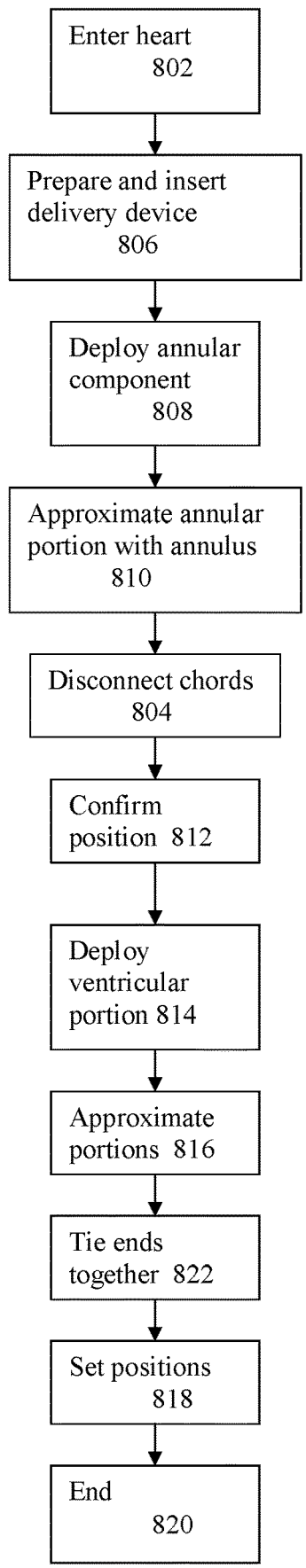
FIG. 6 is a flowchart of a method of deploying the prosthetic mitral valve, in accordance with an exemplary embodiment of the invention.

FIG. 6 is a flowchart of a method for deploying a prosthetic mitral valve, using the deployment device, in accordance with an exemplary embodiment of the invention. Optionally, the trans-apical approach is used. However, the method is applicable to other approaches, for example, trans-vascular approaches through the aorta into the left ventricle. To help understand the method, reference will also be made to FIGS. 4A-4H which graphically illustrate the method as applicable to self-expanding annulus part 52 and ventricle part 54. To help understand the method, reference will also be made to FIGS. 5A-5G which illustrate the method as applicable to annulus part 52 and ventricle part 54 that are expandable to application of an outward radial force.

In some embodiments, at least some of the procedure is performed under fluoroscopic guidance.

Optionally, at 802 and/or at 4A, access to the heart is obtained, for example, by apex 48 puncture. Alternatively, access to the heart is obtained using a vascular approach, for example, obtaining access in the femoral artery, and threading a guidewire and/or catheter to the heart through the aorta, or from the femoral artery, into the right atrium, and after making a septal puncture to the left atrium. Optionally, a guide wire 100 (e.g., soft and/or flexible) is passed retrograde across native mitral valve 26 (e.g., regurgitant or other defects).

Optionally, at 806, delivery device 74 and/or 106 is prepared. Optionally, cap 98 of deployment device 74 is removed. Optionally or additionally, the preservative solution is washed out of delivery lumen 78. Optionally or additionally, the solution is replaced with saline while ensuring adequate degassing of delivery lumen 78.

Figure 4A:
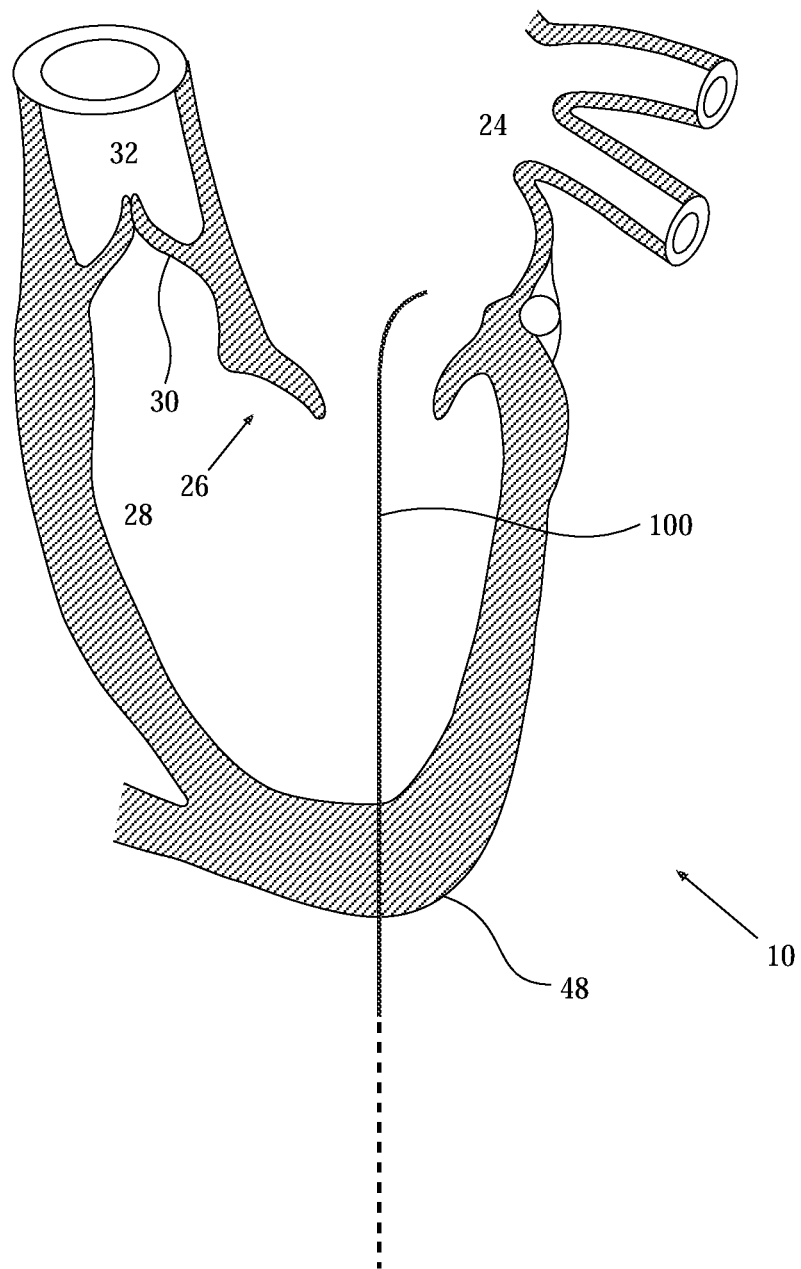
FIGS. 4A-4H depict the deployment of a prosthetic mitral valve using the deployment device of FIG. 3, in accordance with an exemplary embodiment of the invention.
Figure 4B:
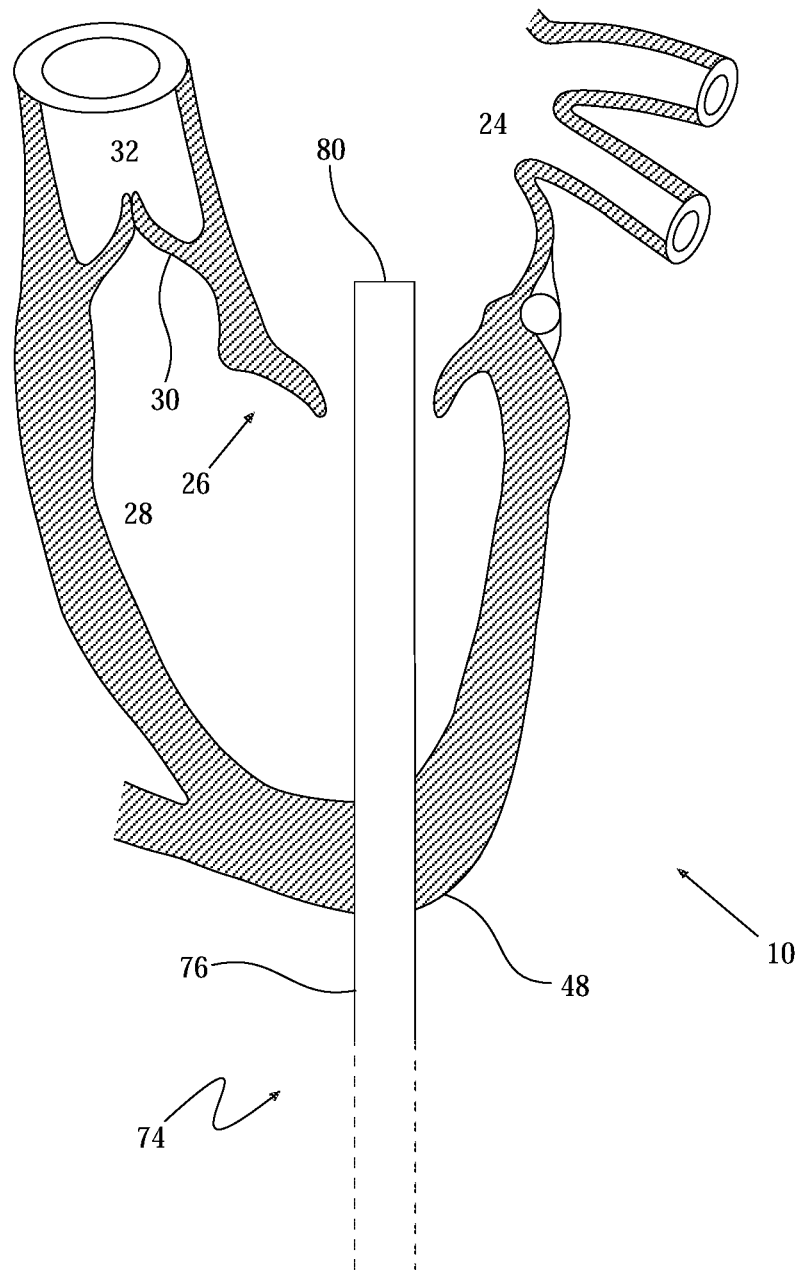

In some embodiments, deployment device 74 is guided distal end first along guide wire 100 until distal opening 80 is located inside left atrium 24, for example, across mitral annulus 34. Optionally, guide wire 100 is withdrawn (FIG. 4B, FIG. 5A).

Figure 4C:
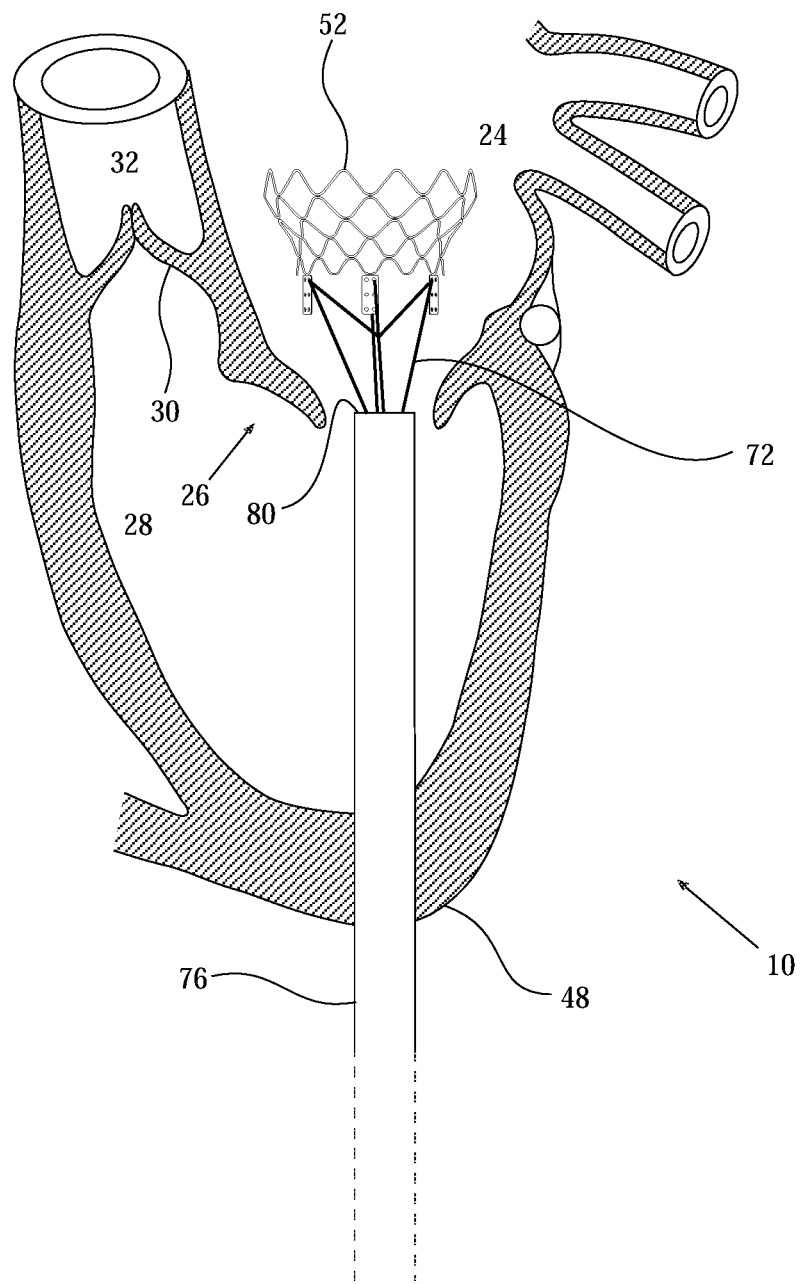

At 808 and/or FIG. 4C, the annular component is deployed. Optionally, push rod 90 (see back to FIG. 3) is pushed distally to function as an annulus-part release component. Optionally, rod 90 pushes annulus part 52 out of delivery housing 76, for example, through distal opening 80, into the volume of left atrium 24.

In some embodiments, once released from the confines of delivery housing 76, annulus part 52 self-expands to adopt a deployed configuration inside left atrium 24. In some embodiments, annulus part 52 remains associated with delivery housing 76, for example, through filament 72.

Alternatively in some embodiments, as shown in FIG. 5B, rigid balloon inflation tube 108 is pushed forward to function as an annulus-part release component. Optionally, tube 108 carries annulus part 52 crimped on distal balloon 110 out of delivery housing 76 into the volume of left atrium 24. Optionally or additionally, tube 108 functions as a ventricle-part release component. Optionally, tube 108 carries ventricle part 54 crimped on proximal balloon 112 out of delivery housing 76 into the volume of left ventricle 28.

In some embodiments, inflation fluid (e.g., saline) is forced through one lumen of balloon inflation tube 108, inflating distal balloon 110 and thereby expanding annulus part 52 inside left atrium 24. In such embodiments, distal balloon 110 functions as a component of an annulus-part expansion assembly. Optionally, the inflation fluid is withdrawn, deflating distal balloon 110 (FIG. 5C).

In some embodiments, the annulus part 52 comprises one or more piercing elements adapted to pierce the leaflets, for example, upon expansion of annulus part 52. Alternatively or additionally, the piercing elements are adapted to pierce surrounding tissues, for example, the fibrous ring and/or the atrium wall. Not necessarily limiting examples of piercing elements include: barbs, hooks, needles. Potentially, the piercing elements help anchor annulus part 52 to the leaflets and/or surrounding tissues.

Figure 4D:
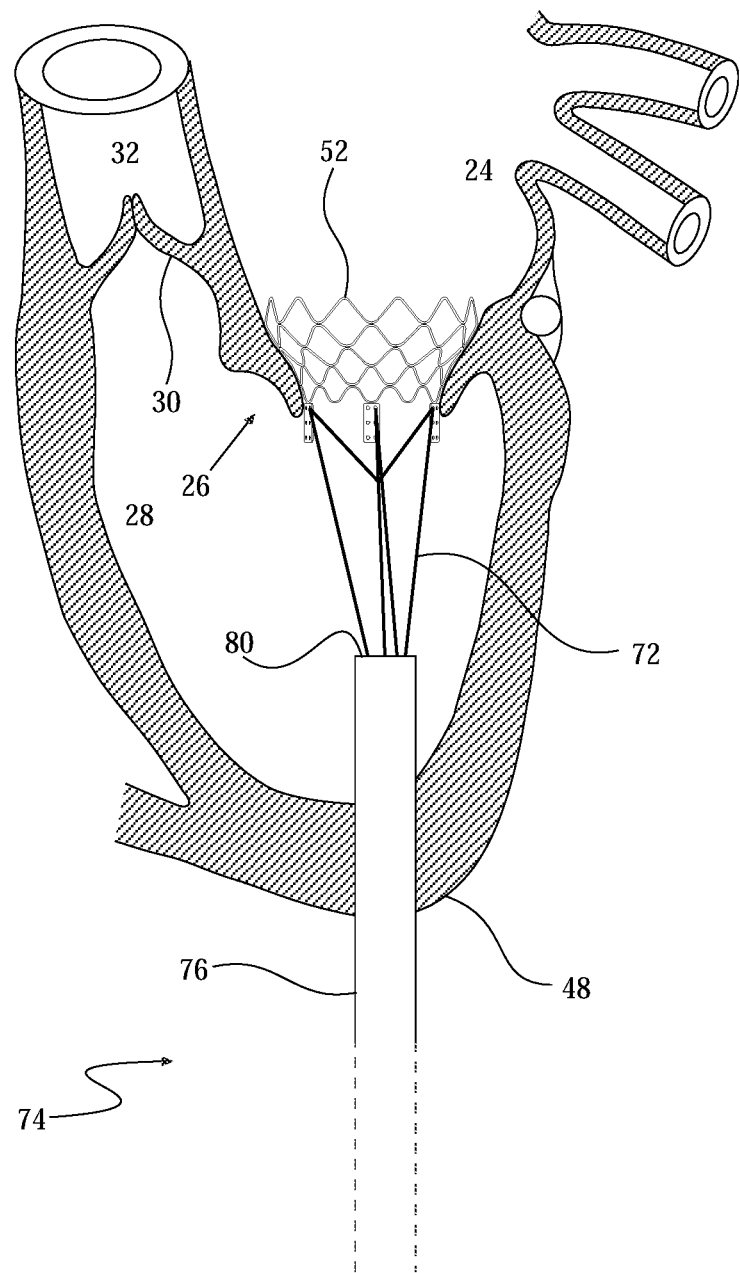

At 810 and/or FIG. 4D, the annular component is approximated with the native mitral valve annulus.

In some embodiments, deployment device 74 is withdrawn in a proximal direction so that distal opening 80 is located inside left ventricle 28.

Optionally, proximal end 94 of filament 72 is pulled proximally so that filament 72 functions as an annulus-part placement component, pulling annulus part 52 to a properly deployed position in mitral valve annulus 34.

Optionally, proximal portion 62 of annulus part 54 is directed into mitral valve annulus 34. Optionally or additionally, a portion thereof (e.g., tabs 58) passes through mitral valve annulus 34, into left ventricle 28, and optionally past the edges of mitral valve leaflets 38 and 40.

Alternatively, in some embodiments as shown in FIG. 5D, proximal end of filament 72 is pulled proximally through the proximal end of delivery housing 76 while balloon inflation tube 108 is held in place. In such embodiments, filament 72 functions as the annulus-part placement component, pulling annulus part 52 to a properly deployed position in mitral valve annulus 34.

Optionally at 812, the position of annulus part 52 in mitral valve annulus 34 is confirmed, for example, by imaging (e.g., fluoroscopy, ultrasound).

Optionally, at 804, the chordae are disconnected from papillary muscles (both not depicted in FIG. 4 for clarity), for example by cutting with a tool that is guided along guide wire 100 or is inserted through the apex incision, such as a knife.

In practice, once the annular component has been deployed, leaflets will remain in the ventricle even if cords are removed, as the leaflets will be held in position by the annular part against the mitral valve annulus, being prevented from prolapsing back into the atrium by the annular component. Alternatively, some of the cords are disconnected and some are left intact, for example, if using the ventricle component that is a partial ring.

Alternatively, in some embodiments, the chords are not cut. Optionally, the embodiment of the partial-circumference ventricle component is used.

Figure 4E:
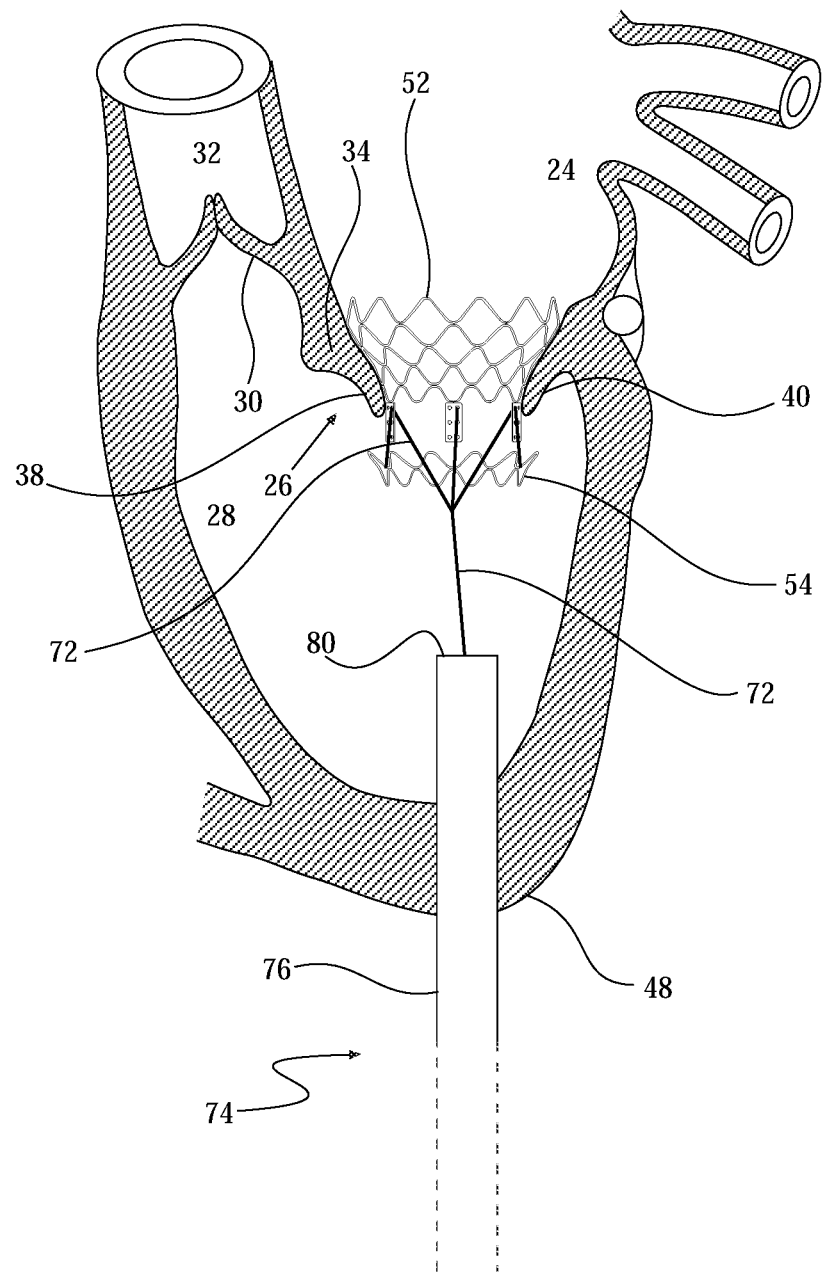

At 814 and/or FIG. 4E, the ventricular component is deployed. Optionally, filament 72 (e.g., proximal end 94 thereof) is pulled proximally to function as a ventricular-part release component. Optionally, filament 72 pulls ventricle part 54 out of delivery housing 76, for example, through distal opening 80 into the volume of left ventricle 28.

In some embodiments, once released from the confines of delivery housing 76, ventricle part 54 self-expands to adopt a deployed configuration inside left ventricle 28.

Alternatively, in some embodiments and as illustrated in FIG. 5E, inflation fluid is forced through the second lumen of balloon inflation tube 108, inflating proximal balloon 112 and thereby expanding ventricle part 54 inside left ventricle 28. In such embodiments, proximal balloon 112 functions as a component of the ventricle-part expansion assembly. Optionally, the inflation fluid is withdrawn, deflating proximal balloon 112.

Figure 4F:
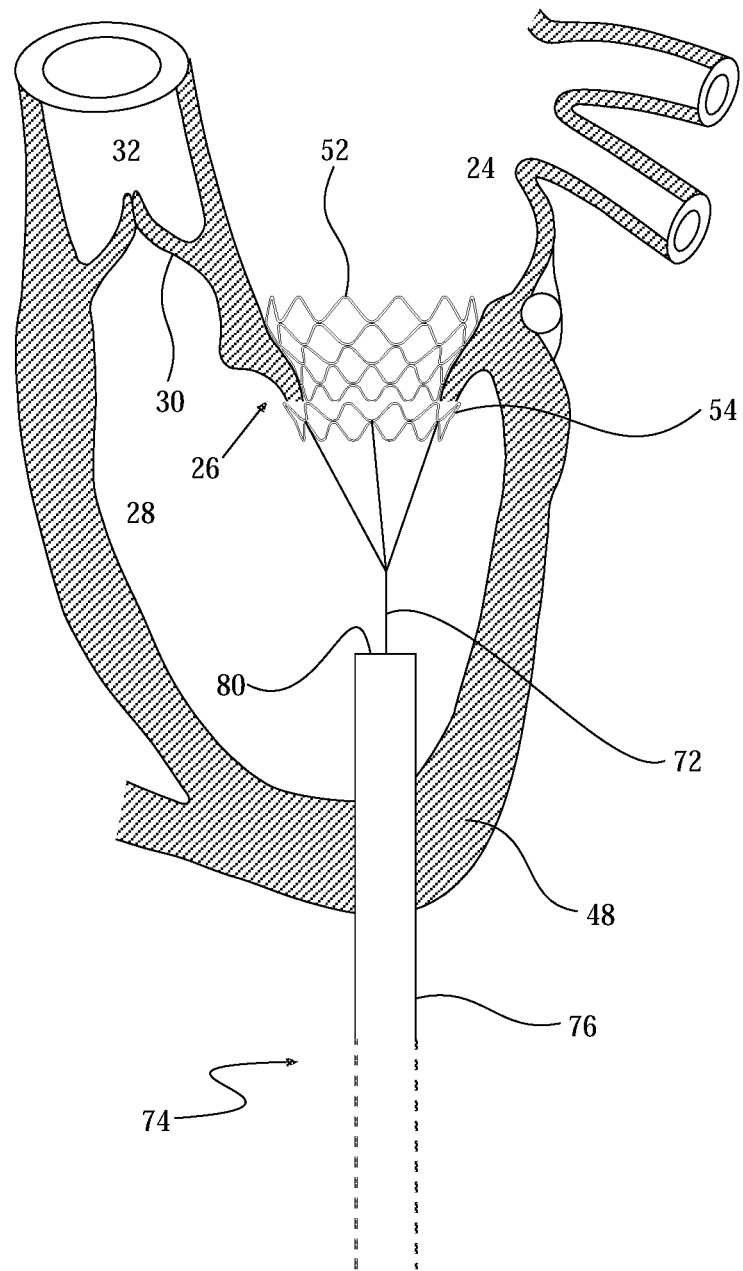

At 816 and/or FIG. 4F or FIG. 5F, the annular and ventricle portions are approximated.

Optionally in some embodiments, the approximation is performed by an approximating and/or joining component. Optionally, proximal end 94 of filament 72 is pulled proximally even further than in box 814. Optionally, filament 72 functions as an approximating component, positioning annulus part 52 and ventricle part 54 in close proximity. Optionally or additionally, filament 72 functions as a joining component, pulling ventricle part 54 over at least a portion of mitral valve leaflets 38 and/or 40 and/or over proximal portion 62 of annulus part 52. Optionally or additionally, ventricle part 54 at least partially encircles portions of proximal portion 62 of annulus part 52, (e.g., tabs 58) as well as mitral valve leaflets 38 and/or 40.

In some embodiments, one filament branches out into multiple attachment locations on annulus 52. Potentially, pulling on the one filament moves and/or approximates annulus 52 with ventricle 54. Alternatively, each attachment location is associated with an independent filament, and each filament requires pulling. Potentially, the multiple filaments allow increased control over the approximation, as pulling the different filaments associated with locations around annulus 52 can tilt the valve, or move the valve in a radial direction.

In some embodiments, the pulling anchors the prosthetic valve to leaflets 38 and/or 40 between ventricle part 54 and annulus part 52 (e.g., proximal portion 62).

Alternatively, in some embodiment, the approximation is performed by using one or more balloons (note that the balloons can be used even in embodiments in which ventricle part 54 and/or annulus part 52 are self-expanding). Optionally, a first balloon is expanded inside the expanded annuls part 52. In the embodiment in which annulus part 52 is funnel shaped, the first balloon prevents distal movement of annulus part 52 into the left ventricle. Optionally or additionally, a second balloon is expanded inside the expanded ventricle part 54. Optionally, the second balloon is wider proximally, wider than the diameter of ventricle part 54, to prevent distal movement of ventricle part 54 into the left ventricle. Optionally, the expanded balloons are used to guide and/or move the annulus part 52 and/or ventricle part 54. For example, the operator can proximally pull the first balloon and distally push the second balloon, thereby approximating annulus part 52 and ventricle part 54.

Optionally, at 822, filaments 72 are tied together, in accordance with some embodiments of the invention. Optionally, filament 72 is prearranged for easy tying, for example, having a pre-existing knot that requires tightening to secure the tying.

Figure 4G:
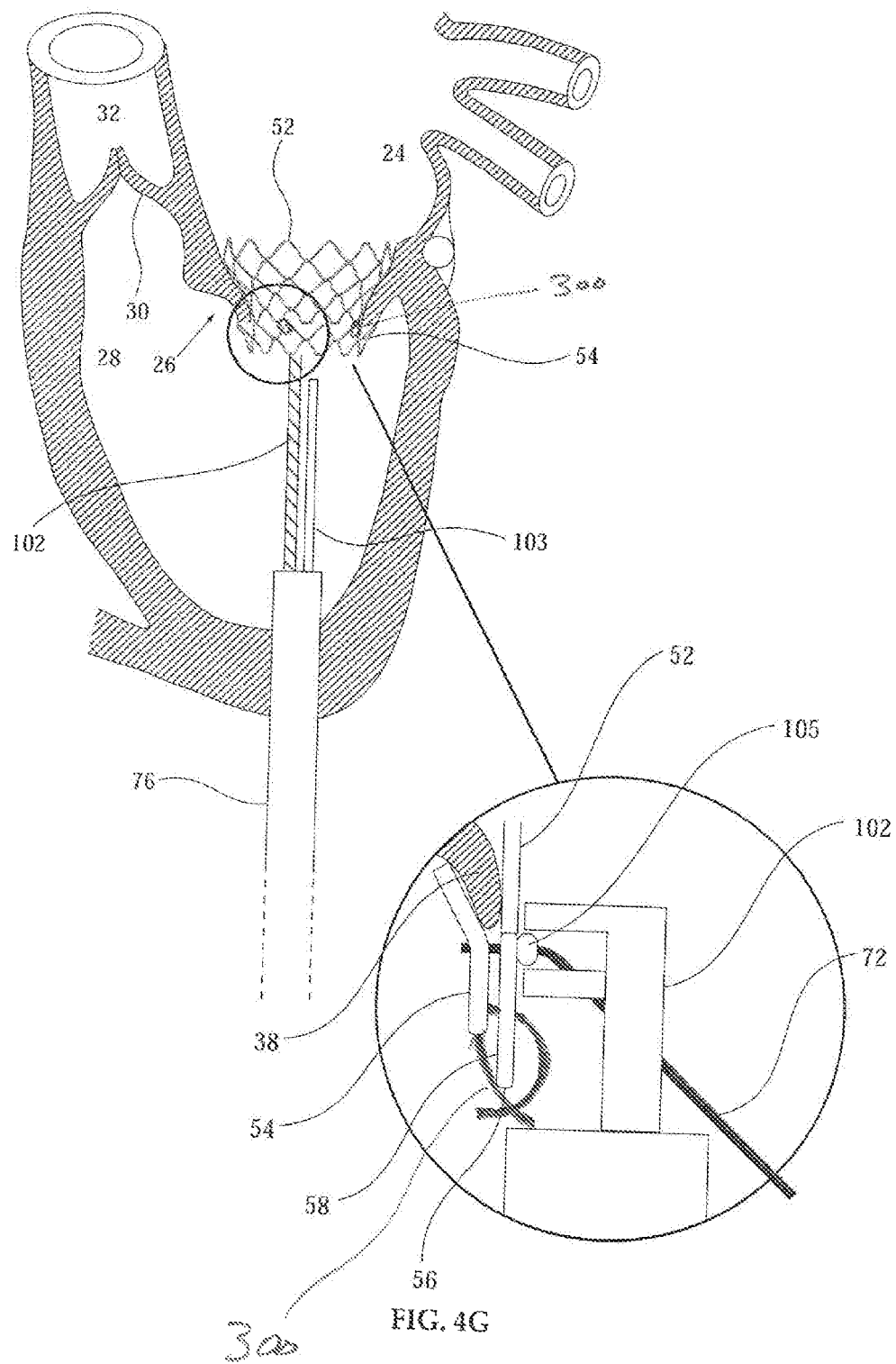
Figure 4H:
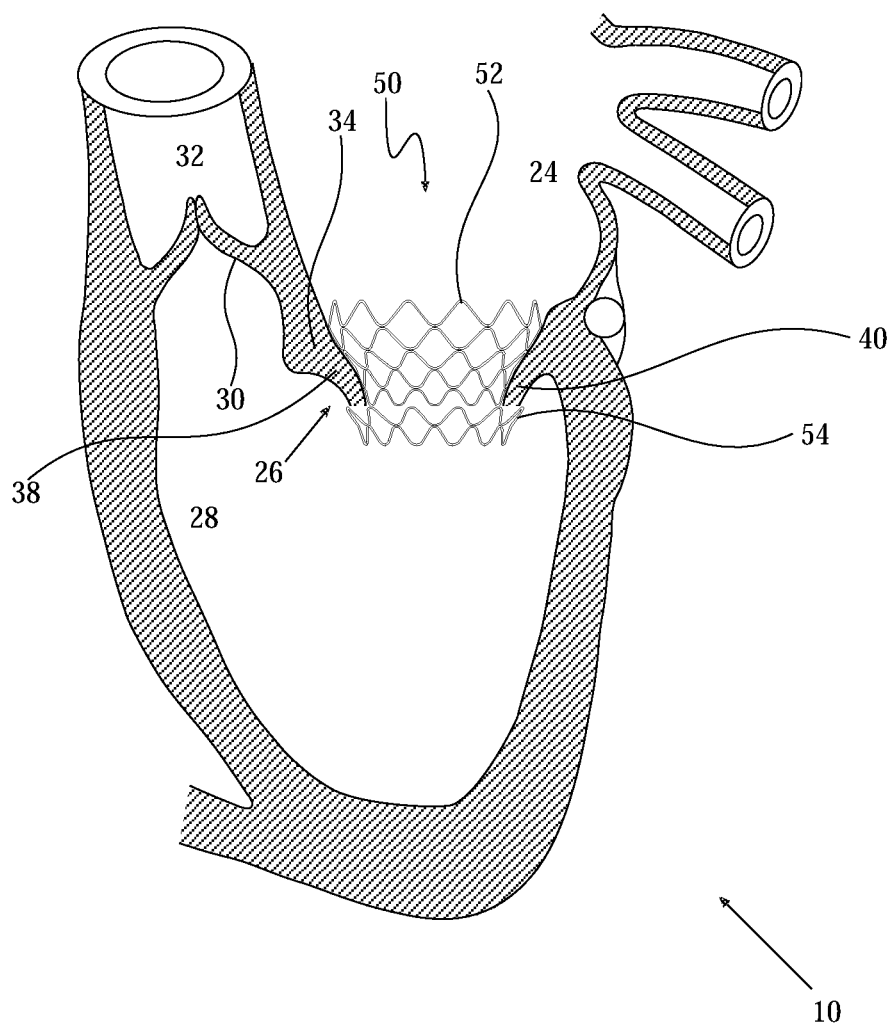

Optionally, at 818 and/or FIG. 4G, the relative positions of atrial part 52 and ventricle part 54 are set so that relative movement is reduced and/or prevented.

In some embodiments, ventricle part 54 comprises one or more piercing elements adapted to pierce the leaflets. Optionally or additionally, the piercing elements are adapted to pierce surrounding tissues, for example, the fibrous ring and/or ventricle wall. Optionally, the piercing occurs upon moving ventricle part 54 towards atrial part 52. Potentially the piercing elements help to grab on to the leaflets, and help to set the relative positions of atrial part 52 and ventricle part 54.

Optionally, balloon inflation tube 108 is withdrawn from delivery housing 76 in a proximal direction.

Optionally, a crimping tool 102 (e.g., surgical clamp) and/or video camera 103 (e.g., fiber-optic) are advanced into delivery lumen 78, for example, through suitable ports in sealing ring 92 of deployment device 76, and/or through a different access route (e.g., through the vasculature using trans-catheter techniques). Optionally, crimping tool 102 is advanced to proximity with ventricle part 54, for example, through delivery lumen 78 of delivery housing 76. Optionally, tool 102 (e.g., under guidance of a fiber-optic video camera 103 and/or echo and/or fluoroscopy) is used to crimp connectors 105 (e.g., 1, 3, 5, or other numbers) around the distal ends of filament 72 (e.g., 1, 3, 5, or other numbers) (e.g., near the inner face of tabs 58). Optionally, the crimping fixes the relative positions between annulus part 52 and ventricle part 54. Alternatively or additionally, tool 102 is used to crimp attachment elements 300, for example, by bending the fingers of elements 300 so that the edges of the fingers overlap one another and 'grab' the struts of ventricle part 54.

Optionally crimping tool 102 and/or video camera 103 are withdrawn from the delivery lumen of delivery housing 76.

Optionally, a cutting tool is inserted and is used to clip the distal ends of filament 72, for example, close to crimped connectors 105. Optionally, the cutting tool and the thus-released portion of filament 72 are withdrawn from left ventricle 28 in a proximal direction. Alternatively, filament 72 remains secured to deployed prosthetic mitral valve 104. Optionally, proximal end 94 trails out of heart 10 through the incision in apex 48. Optionally, the incision is closed in the usual way.

In some embodiments, filament 72 remains secured to deployed prosthetic mitral valve 104 with proximal end 94 trailing out of heart 10 through the incision in apex 48. Optionally, proximal end 94 of filament 72 is secured, for example, to a pad 114 that contacts outer surface 116 of heart 10, for example, commercially-available pads with the Coapsys® device from Myocor, Inc., Maple Grove, Minn., USA. In some embodiments, filament 72 functions as a tether, assisting in preventing prosthetic mitral valve 104 from moving into left atrium 24, (FIG. 5G).

Optionally, at 820 and/or FIG. 8H, the procedure is ended. Optionally, delivery housing 76 is withdrawn from heart 10.

In some embodiments, prosthetic mitral valve 50 is deployed in heart 10, surrounding native mitral valve annulus 34, grabbing at least some of leaflets 38 and/or 40 from above with annulus part 52 and from below with ventricle part 54.

Once the operation is complete, deployed prosthetic mitral valve 50 functions as a patent mitral valve. Potentially, the self-expanding properties of annulus part 52 and/or ventricle part 54 allow dynamic conformation to the shape and/or size of mitral valve annulus 34 and/or the atrial walls as these change during the beating of heart 10, potentially allowing parts 52 and/or 54 to adopt a smaller configuration when mitral valve annulus 34 compresses and/or to spring back to a larger-sized configuration when mitral valve annulus 34 relaxes.

In the embodiment discussed above with reference to FIGS. 3 and 4, annulus part 52 and ventricle part 54 are self-expanding from a delivery configuration to a deployed configuration. In some embodiments, one or both of an annulus part and a ventricle part of a prosthetic mitral valve as described herein are expandable from a delivery configuration to a deployed configuration by application of a radially outward force applied to an inner surface thereof. In a not necessarily limiting example, the radially expandable portions are made for example, from steel 316L. Specifically, in some embodiments, an annulus part is self-expanding and a ventricle part is expandable by application of an outwards radial force. In a not necessarily limiting example, the radially expandable portion is made for example from steel, and the self-expanding portion is made for example from Nitinol, with the portions attached together, for example, by welding, gluing, crimping or other methods. Alternatively, a ventricle part is self-expanding and an annulus part is expandable by application of an outwards radial force. Alternatively, both an annulus part and a ventricle part are expandable by application of an outwards radial force. Alternatively, annulus and/or ventricle parts are not expandable, for example, for surgical implantation. In such a case, other materials can be used, for example, polyurethane.

In some embodiments, the method of FIG. 6 is used to deliver the radially expandable embodiments of annulus part 52 and ventricle part 54. In FIGS. 5A-5G are depicted the deployment of a prosthetic mitral valve as described herein, prosthetic mitral valve 104, that is substantially similar to prosthetic mitral valve 50 described above except that both an annulus part 52 and a ventricle part 54 are expandable by application of an outwards radial force. In some embodiments, deployment is performed using an embodiment of a deployment device as described herein, deployment device 106, Optionally, at 802, deployment begins as described above for prosthetic mitral valve 50. Optionally, deployment device 106 is advanced so that distal opening 80 is located in left ventricle 28 across mitral valve annulus 34, FIG. 5A.

At 808, (e.g., rigid) balloon inflation tube 108 is pushed forward to function as an annulus-part release component. Optionally, tube 108 carries annulus part 52 (e.g., crimped on distal balloon 110) out of delivery housing 76 into the volume of left atrium 24.

At 810, a proximal end of filament 72 is pulled proximally (e.g., through the proximal end of delivery housing 76) while balloon inflation tube 108 is held in place. Optionally, filament 72 functions as an annulus-part placement component, by pulling annulus part 52 to a properly deployed position in mitral valve annulus 34, FIG. 5D.

At 814, tube 108 also functions as a ventricle-part release component, carrying ventricle part 54 (e.g., crimped on proximal balloon 112) out of delivery housing 76 into the volume of left ventricle 28, FIG. 5B.

At 816, a proximal end of filament 72 is pulled proximally (e.g., through the proximal end of delivery housing 76) while delivery housing 76 is held in place. Optionally, filament 72 functions as a joining component, bringing annulus part 52 and ventricle part 54 together, by pulling ventricle part 54 over mitral valve leaflets 38, 40 and/or the proximal portion of annulus part 52, FIG. 5F.

At 818, optionally balloon inflation tube 108 is withdrawn from delivery housing 76 in a proximal direction. Optionally, a crimping tool is used to crimp connectors (e.g., three) around the distal ends of filament 72 (e.g., three) near the inner face of tabs 58. The crimping mutually fixing annulus part 52 and ventricle part 54.

At 820, optionally delivery housing 76 is withdrawn from heart 10.

In some of the embodiment of the method described above, a crimping tool 102 and/or a video camera 103 were advanced through delivery lumen 78 of deployment device 74 to assist in deploying a prosthetic mitral valve. Alternatively, one or more of crimping tools, video cameras, and/or other devices for assisting in deploying a prosthetic mitral valve as described herein are brought to a desired location through a different access routes, for example, through the vasculature and into the heart through the aorta, for example, using a suitable catheter.

In some of the embodiments described above, a prosthetic mitral valve includes a valve mechanism that is not subject to prolapse of leaflets into the left atrium, whether due to the particular construction of the valve mechanism or due to the presence of a prolapse-preventing component. In some, non-depicted, embodiments, a prosthetic mitral valve as described herein includes a prolapse-preventing component that is substantially an artificial chorda, for example as described in WO 2009/134701. In some such embodiments, the artificial chordae are deployed substantially as described for a tether (in some embodiments instead of a tether, in some embodiments together with a tether), with the required differences as are clear to a person skilled in the art. Specifically, in such embodiments, the device further comprises a leaflet-valve mechanism functionally associated with the annulus part and at least one artificial chorda having a distal chorda end and a proximal chorda end, the distal chorda end secured to a portion (typically an edge) of at least one leaflet of the leaflet-valve mechanism and the proximal chorda end configured for securing in proximity of the apex of a heart in which deployed, for example, secured to an anchor engaging heart muscle tissue, or passing through the heart muscle and being anchored in place with a pad that presses against an outer wall of the heart. The chorda is configured (including the length thereof) so that motion of the leaflet edge towards the left ventricle is substantially uninhibited, but that prolapse of the leaflet edge into the left atrium is substantially prevented.

In some of the embodiments described above, the ventricle part of a prosthetic mitral valve is configured to at least partially encircle native mitral valve leaflets and is deployed at least partially encircling the native mitral valve leaflets. In some embodiments, the ventricle part of a prosthetic mitral valve is not necessarily configured to encircle native mitral valve leaflets and/or is not deployed at least partially encircling the native mitral valve leaflets. In some such embodiments, when deployed the ventricle part of such an embodiment of a prosthetic mitral valve encircles the proximal portion of the annulus part and. of necessary, is fixed thereto. By virtue of having a larger diameter than the diameter of the mitral valve annulus (especially during atrial systole), such a ventricle part cannot pass through the mitral valve annulus and thereby prevents the prosthetic mitral valve from moving into the left atrium, especially because the mitral valve annulus constricts during ventricular systole when there is the greatest possibility of such movement.

In the embodiments described above, the teachings herein are implemented to provide a prosthetic heart valve that is a prosthetic mitral valve, having features rendering the prosthetic heart valve exceptionally useful for overcoming challenges in the field of prosthetic mitral valve deployment. In some, non-depicted, embodiments, the teachings herein are implemented, with the required changes, to provide a prosthetic heart valve that is a prosthetic aortic valve.

In some embodiments, at least one of the annulus part and the ventricle part of a prosthetic mitral valve as described herein includes bending mating features, configured to be bent (in this context bent being an adjective, not a verb) when the annulus part and the ventricle part are mated (in this context, mated being an adjective not verb). For example, in some embodiments similar to valves 50 and 104, the three distal ends of filament 72 passes through gaps such as slots in the structure of ventricle part 52 and are secured to bendable tabs (integrally formed or connected) that can pass into the gaps in annulus part. In such an embodiment, the gaps and the bendable tabs are mating features. When the proximal end of filament 72 is pulled to join annulus part 52 and ventricle part 54, the bendable tabs are pulled to pass into the gaps, so that the two parts are mated. With further pulling of the proximal end of filament 72, the bendable tabs are bent downwards, locking annulus part 52 and ventricle part 54 together. Subsequently, filament 72 can be cut as described with reference to prosthetic mitral valve 50 or anchored to function as a tether as described with reference to prosthetic mitral valve 104.

Any suitable combination of materials and methods of manufacture may be used in implementing the teachings herein. For example, a person having ordinary skill in the art of prosthetic cardiac valves is able to select suitable materials and methods of manufacture, for example, with reference to commercially-available prosthetic cardiac valves.

The dimensions of the various parts and components of the prosthetic mitral valves and the deployment devices as described herein are any suitable dimensions, and can be determined by a person having ordinary skill in the art, for example, with reference to commercially-available transapical delivery devices and accompanying prosthetic cardiac valves, especially prosthetic mitral valves, for example the Perimount™ Magna prosthetic mitral heart valve by Edwards Lifesciences LLC (Irvine, Calif., USA).

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Citation or identification of any reference in this application shall not be construed as an admission that such reference is available as prior art to the invention.

Section headings are used herein to ease understanding of the specification and should not be construed as necessarily limiting.

What is claimed is:

1. A method comprising:
deploying an expandable prosthetic mitral valve device in a heart of a subject, by:
 deploying a first component of the prosthetic mitral valve device in a left atrium of the subject, the first component including an annulus part that is deployed at least partially in a vicinity of a native mitral annulus of the subject;
 deploying a second component of the prosthetic mitral valve in a left ventricle of the subject, the second component including a ventricular part,
  deployment of the first component and the second component being performed such that there is a gap between the ventricular part and the annulus part, the gap being configured to accommodate one or more leaflets of the native mitral valve;
 approximating the first and second components with respect to each other, such that, when the first and said second components are in an approximated configuration with respect to each other, the one or more leaflets of the native mitral valve are trapped within the gap between the ventricular part and the annulus part; and
 securing the annulus part and the ventricular part in the approximated configuration.

2. The method according to claim 1, wherein approximating the first and second components with respect to each other comprises approximating the first and second components with respect to each other by pulling a wire connecting said first and second components.

3. The method according to claim 1, further comprising piercing the leaflets of the native mitral valve by at least one of said first or said second components.

4. The method according to claim 1, further comprising piercing tissue surrounding the leaflets of the native mitral valve by at least one of said first or said second components.

5. The method according to claim 1, wherein approximating the first and second components with respect to each other comprises pulling the ventricular part toward the annulus part such that the ventricular part at least partially encircles both a portion of the annulus part and the one or more leaflets of the native mitral valve.

6. The method according to claim 1, wherein deploying the expandable prosthetic mitral valve device in the subject's heart further comprises deploying the expandable prosthetic mitral valve device in the subject's heart using at least one of a transapical approach and a vascular approach.

7. The method according to claim 1, wherein deploying the expandable prosthetic mitral valve device in the subject's heart further comprises deploying the expandable prosthetic mitral valve device in the subject's heart using a transseptal approach.

8. The method according to claim 1, wherein the annulus part includes a valve mechanism suitable for functioning as a prosthetic mitral valve.

9. The method according to claim 1, wherein approximating the first and second components with respect to each other comprises approximating the first and second components with respect to each other using at least one elongated tether having a first end functionally associated with the annulus part and a second end configured for securing in proximity of an apex of the subject's heart, so that a force applied to said second end of said tether is at least partially transferred by said annulus part to an atrial surface in a vicinity of the subject's native mitral valve annulus.

10. The method according to claim 1, wherein approximating the first and second components with respect to each other comprises approximating the first and second components with respect to each other using at least one elongated tether having a first end functionally associated with said ventricular part and a second end configured for securing in proximity of an apex of said heart, wherein a portion of said tether passes through said annulus part so that force applied to the second end of the tether pulls the ventricular part towards said annulus part, and is at least partially transferred by the annulus part to an atrial surface in a vicinity of the subject's native mitral valve annulus.

11. The method according to claim 1, wherein at least one of said annulus part and said ventricular part includes mating features, and wherein approximating the first and second components with respect to each other comprises bending the mating features.

12. The method according to claim 1, wherein approximating the first and second components with respect to each other comprises approximating the first and second components with respect to each other using a deployable tether.

13. The method according to claim 1, wherein approximating the first and second components with respect to each other comprises approximating the first and second components with respect to each other using a plurality of filaments each of which extends from the deployment device at one filament end to another filament end that is secured to the ventricular part, each of the filaments contacting a region of slidable association with the annulus part between the filament ends.

14. The method according to claim 13, wherein approximating the first and second components with respect to each other comprises approximating the first and second components with respect to each other using a plurality of filaments that are releasably secured to said ventricular part.

15. The method according to claim 13, wherein approximating the first and second components with respect to each other comprises approximating the first and second components with respect to each other using a plurality of filaments that are fixedly secured to said ventricular part.

\* \* \* \* \*